(12) United States Patent
Stamler

(10) Patent No.: US 11,426,386 B2
(45) Date of Patent: Aug. 30, 2022

(54) COMPOSITIONS AND METHODS OF MODULATING S-NITROSYLATION

(71) Applicant: CASE WESTERN RESERVE UNIVERSITY, Cleveland, OH (US)

(72) Inventor: Jonathan S. Stamler, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 0 days.

(21) Appl. No.: 16/283,226

(22) Filed: Feb. 22, 2019

(65) Prior Publication Data

US 2019/0183861 A1 Jun. 20, 2019

Related U.S. Application Data

(63) Continuation-in-part of application No. PCT/US2018/052214, filed on Sep. 21, 2018, and a continuation-in-part of application No. 15/533,268, filed as application No. PCT/US2015/064308 on Dec. 7, 2015.

(60) Provisional application No. 62/633,901, filed on Feb. 22, 2018, provisional application No. 62/562,784, filed on Sep. 25, 2017, provisional application No. 62/088,002, filed on Dec. 5, 2014.

(51) Int. Cl.
*A61K 31/4166* (2006.01)
*A61P 9/00* (2006.01)
*A61K 31/4184* (2006.01)

(52) U.S. Cl.
CPC ............ *A61K 31/4184* (2013.01); *A61P 9/00* (2018.01); *A61K 31/4166* (2013.01)

(58) Field of Classification Search
CPC .............................. A61K 31/4166; A61P 9/00
See application file for complete search history.

(56) References Cited

U.S. PATENT DOCUMENTS

| | | | |
|---|---|---|---|
| 2,683,718 A | 7/1954 | Dornfeld et al. | |
| 5,153,211 A | 10/1992 | York, Jr. | |
| 7,674,795 B2 | 3/2010 | Mailliet et al. | |
| 2007/0275907 A1* | 11/2007 | Chen ..................... | C07D 311/96 514/23 |
| 2010/0272711 A1* | 10/2010 | Feldman .............. | A61K 31/437 424/130.1 |
| 2010/0292178 A1 | 11/2010 | Young | |
| 2010/0305078 A1 | 12/2010 | Schotzinger et al. | |
| 2011/0092566 A1 | 4/2011 | Srivastava et al. | |
| 2012/0220001 A1 | 8/2012 | Marlière | |
| 2013/0196342 A1 | 8/2013 | Stamler et al. | |
| 2014/0206693 A1 | 7/2014 | Srivastava et al. | |

FOREIGN PATENT DOCUMENTS

| | | |
|---|---|---|
| EP | 1961420 A1 | 8/2008 |
| EP | 1987829 A1 | 11/2008 |
| WO | 2002/047680 A2 | 6/2002 |
| WO | 2004/110488 A1 | 12/2004 |
| WO | 2008/118370 A2 | 10/2008 |
| WO | 2010/104595 A1 | 9/2010 |
| WO | 2016090373 A1 | 6/2016 |

OTHER PUBLICATIONS

Hwang et al. FASEB J., 2004, vol. 18, No. 11, pp. 192-199.*
Weiss et al. Nat. Chem. Biol.,2007, vol. 3, Issue 2, pp. 739-744.*
Meyler's Side Effects of Drugs, Sixteenth Ediction, 2016, General Information, p. 1.*
Hwang et al. The FASEB Journal, Published online Dec. 2001, pp. 1-22.
Supplemental European search report for application No. 15864966.5-1112/3226859, dated Nov. 30, 2018.
Suropean Search Report for application No. 15864966.5-1112/3226859.
Tao B et al: "Synthesis of Conformationally Constrained Spirohydantoins With a Dibenzoaa, Doheptadiene Ring", Synthesis, Georg Thieme Verlag, Stutigart, DE, No. 10, Feb. 29, 2000, pp. 1449-1453.
Partial Supplementary European Search Report for Application No. 15864966.5-1112/3226859.
Puneet Anand, "Purification and Characterization of Novel Denitrosylases from Yeast and Mammals", Dec. 31, 2012, pp. 1-156.
Puneet Anand et al., "Identification of S-nitroso-CoA reductases that regulate protein S-nitrosylation", Proceedings of the National Academy of Sciences, vol. 111, No. 52, Dec. 15, 2014, pp. 8572-18577.
Morakinyo, MK et al., "Detailed mechanistic investigation into the Snitrosation of cystearnine", 26 Can. J. Chem. vol. 90, 2012, pp. 724-738.
Zhang, HH et al., "Estrogen-Responsive nitroso-Proteorne in Uterine Artery Endothelial Cells: Role of Endothelial Nitric Oxide Synthase and Estrogen Receptor-beta", J. Cell Physiol. vol. 227, No. 1, Jan. 2012, pp. 146-159.
Morris, SL et al., "Inhibition of Bacillus cereus Spore Outgrowth by Covalent Modification of a Sulfhydryl Group by Nitrosothiol and Iodoacetate", Journal of Bacteriology, vol. 148, No. 2, Nov. 1981, pp. 465-471.
Soda, M. et al., "Inhibition of Human Aldose Reductase-Like Protein (AKR1810) by alpha- and gamma-Mangostins, Major Components of Pericarps of Mangosteen", Biol. Pharm. Bull. vol. 35, No. 11, 2012, pp. 2075-2080.

(Continued)

*Primary Examiner* — Samira J Jean-Louis
(74) *Attorney, Agent, or Firm* — Tarolli, Sundheim, Covell & Tummino LLP

(57) ABSTRACT

A method of treating cardiovascular disorders and diseases in a subject in need thereof includes administering to the subject an ADH inhibitor, AKR inhibitor, and/or SNO-CoAR inhibitor at an amount(s) effective to promote S-nitrosylation of proteins in the subject, wherein the ADH inhibitor and/or SNO-CoAR inhibitor is not an ADH3 inhibitor.

5 Claims, 11 Drawing Sheets

(56) References Cited

OTHER PUBLICATIONS

Roediger, We, "Review article: nitric oxide from dysbiotic bacterial respiration of nitrate in the pathogenesis and as a target for therapy of ulcerative colitis" Ailment Pharmacol, Ther. vol. 27, 2008, pp. 531-541.
Malatkova, Pet al., "Human Carbonyl Reductases", Current Drug Metabolism, vol. 11, 2010, 24 pp. 639-658.
International Search Report & Written Opinion for International Application No. PCT/US2015/064308.
Jonathan S. Stamler; "Compositions and Methods of Reducing Serum Cholesterol and PCSK9"; U.S. Appl. No. 16/648,737, filed Mar. 19, 2020; U.S. Non-Final Office Action dated Mar. 7, 2022; 11 pgs.
Applicant: Case Western Reserve University; PCT International Application No. PCT/US19/52426, Filed: Sep. 23, 2019; PCT International Search Report and Written Opinion, Authorized Officer: Lee Young; dated Feb. 7, 2020; 9 pgs.
PubChem-CID-10335836, Create Date: Oct. 25, 2006; p. 2.

\* cited by examiner

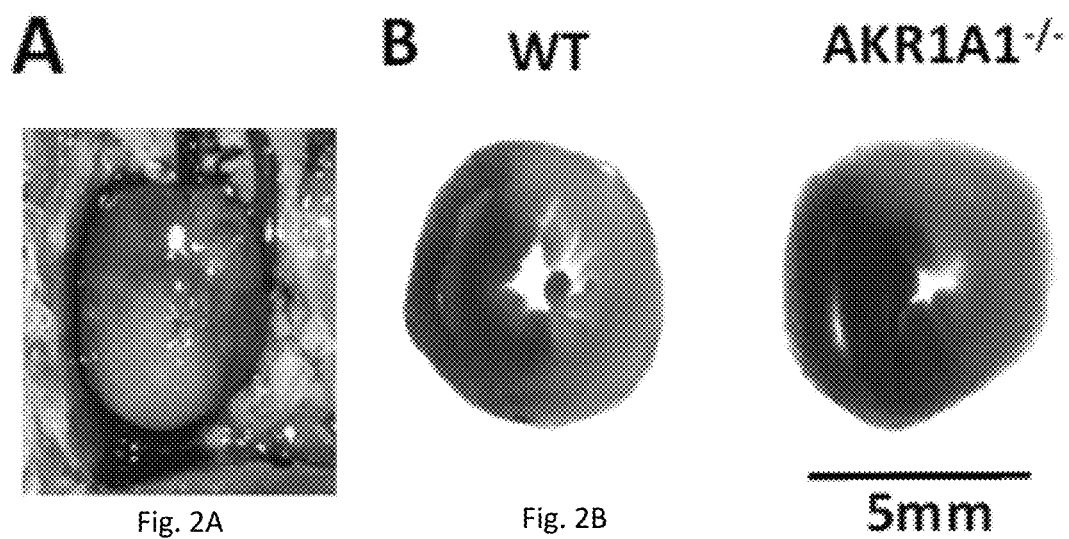
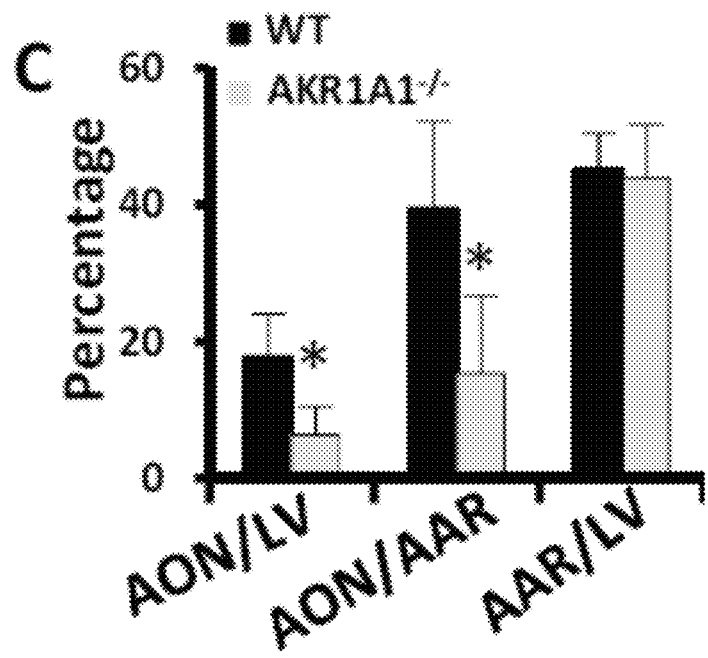
Fig. 2A
Fig. 2B
Fig. 2C

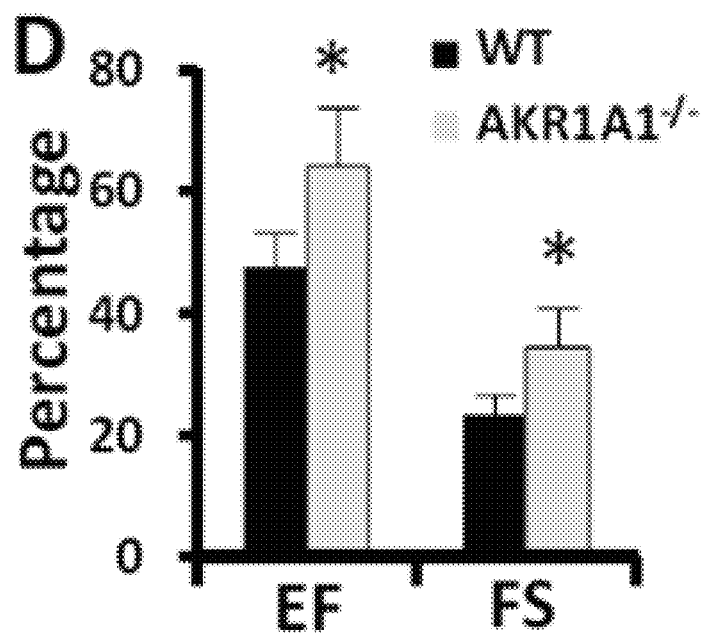
Fig. 2D
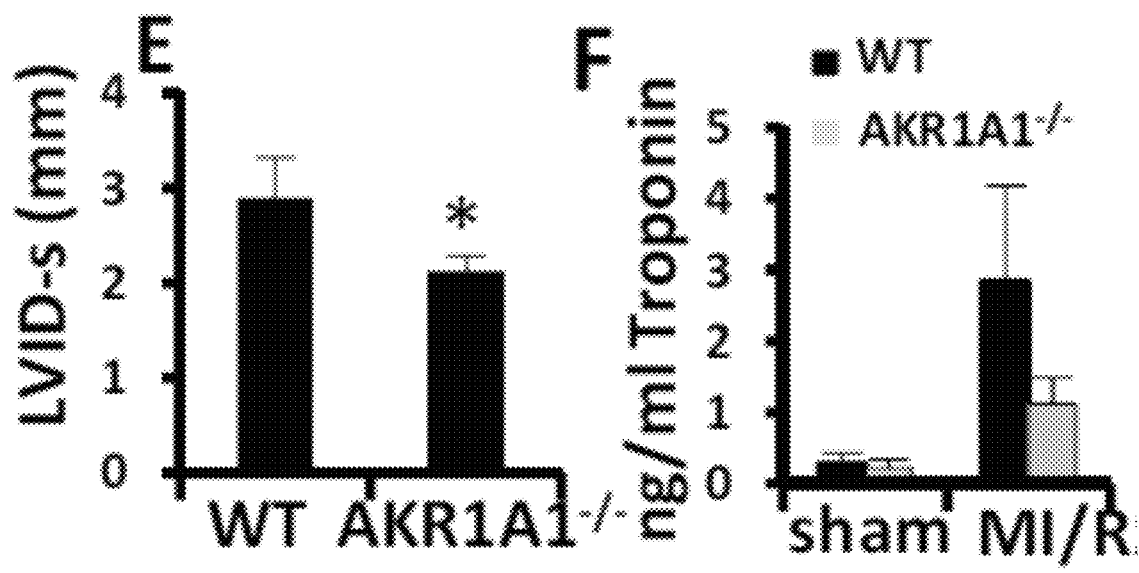
Fig. 2E
Fig. 2F

COMPOSITIONS AND METHODS OF MODULATING S-NITROSYLATION

RELATED APPLICATION

This application claims priority from U.S. Provisional Application No. 62/633,901 filed Feb. 22, 2018, this application is also a Continuation-In-Part of U.S. Ser. No. 15/533,268, filed Jun. 5, 2017, which is a National Phase filing of PCT/US2015/064308, filed Dec. 7, 2015, which claims priority to U.S. Provisional Application Ser. No. 62/088,002, filed Dec. 5, 2014, This application is also a Continuation-In-part of PCT/US2018/052214, filed Sep. 21, 2018, which claims priority to U.S. Provisional Application No. 62/562,784, filed Sep. 25, 2017, the subject matter of which is incorporated herein by reference in its entirety.

TECHNICAL FIELD

This application relates to compositions and methods of modulating protein nitrosylation and particularly relates to the use of alcohol dehydrogenase inhibitors, aldoketo reductase inhibitors, and/or SNO-Coenzyme A reductases inhibitors to enhance protein S-nitrosylation in the heart of a subject and treat cardiovascular disorders and diseases.

BACKGROUND

Myocardial ischemia/reperfusion (MI/R) injury is due to blood restoration after impaired coronary blood supply, which can induce myocardial infarction. Several pathophysiological mechanisms have been suggested to mediate MI/R, including depletion of intracellular ATP, $Ca^{2+}$ overload and excessive reactive oxygen species (ROS) generation, which afterward result in hypercontraction, cytoskeletal fragility, mitochondrial permeability transition, and necrosis or apoptosis of cardiomyocytes. Currently, there is not a definitive intervention to eliminate MI/R-induced myocardial damage.

Nitric oxide (NO) is a gaseous signaling molecule that has pleiotropic effects in the cardiovascular system. NO is synthesized from its precursor L-arginine by a family of NO synthases (NOS), including neuronal (nNOS), inducible (iNOS), and endothelial NOS (eNOS). The low concentrations of NO produced by nNOS and eNOS in heart is considered as a cardioprotective factor due to its vasodilatory, antioxidant, and anti-inflammatory properties, as well as its beneficial effects on cell signaling. However, high concentrations NO produced by iNOS is deleterious to the heart because it causes contractile dysfunction and apoptosis of cardiomyocytes. Cardioprotective functions of NO are mediated by both cyclic guanosine 3',5'-monophosphate (cGMP)-dependent and cGMP-independent mechanisms. NO can activate soluble guanylyl cyclase to generate its second messenger cGMP. Stimulation of cGMP performs the cardioprotetion by beneficial effects on sarcoplasmic reticulum $Ca^{2+}$ oscillations and mitochondrial $Ca^{2+}$ overload. NO also cGMP-independently participates in cardio-protection largely through S-nitrosylation of allosteric and active-site cysteine thiols within proteins. S-nitrosylation of proteins has been demonstrated to affect a broad range of functional parameters, including enzymatic activity, subcellular localization, protein-protein interactions, and protein stability. It is increasingly apparent that disruption of S-nitrosylation is implicated in MI/R, myocardial infarction, cardiac hypertrophy and heart failure. By extension, resolution of aberrant S-nitrosylation and thus restoration of SNO-homeostasis provides an attractive therapeutic target for cardiac disease amelioration.

Reversible S-nitrosylation or denitrosylation of proteins in physiological settings is catalyzed by nitrosylases or denitrosylases respectively. Nitrosylases transfer an NO group from NO, SNO-modified low-molecular-weight thiols, or SNO-protein to Cys thiol side chain of acceptor proteins. By contrast, denitrosylases are enzymes involved in the removal of NO groups from the Cys thiol side chain of proteins or low-molecular-weight thiols. These enzymes ultimately use reducing equivalents derived from NADH or NADPH. In a manner analogous to phosphatases that often set levels of phosphorylation in cells, denitrosylases regulate NO signal transduction by abstracting NO from proteins and setting levels of cellular nitrosylation. More than three thousand proteins are S-nitrosylated across all organ systems. However, there have only been two major classes of denitrosylases identified so far, namely S-nitrosoglutathione (GSNO) reductase (GSNOR) and the thioredoxin (Trx) family of proteins. Particularly, proteomic and targeted analyses have revealed that a large set of cardiac proteins distributed across multiple functional classes are subject to S-nitrosylation, and their modification appears largely independent of the two known denitrosylases GSNOR and Trx.

SUMMARY

Embodiments described herein relate to compositions and methods of modulating protein nitrosylation and particularly relates to the use of alcohol dehydrogenase (ADH) inhibitors (e.g., ADH6 inhibitors), aldoketo reductase (AKR) inhibitors (e.g., AKR1A1 inhibitors), and/or SNO-Coenzyme A reductase (SNO-CoAR) inhibitors (e.g., ADH6 inhibitors and AKR1A1 inhibitors) to increase or enhance protein S-nitrosylation in the heart of a subject and treat cardiovascular disorders and diseases, such as congestive heart failure (CHF), cardiac hypertrophy including both atrial and ventricular hypertrophy, myocardial infarction, myocardial ischemia, myocardial ischemia reperfusion injury, cardiomyopathies, or arrhythmias.

AKR1A1 is a mammalian SNO-CoA reductase, which specifically and efficiently reduces SNO-CoA to CoA by using reducing equivalents of NADPH. AKR1A1 was also found to metabolize GSNO, a known nitrosylating agent. Knockout of AKR1A1 in mice was found to increase cellular protein S-nitrosylation, reduce oxidative stress, and provide cardioprotection against myocardial ischemia reperfusion injury. Inhibition of ADHs (e.g., ADH6), AKRs (e.g., AKR1A1), and/or SNO-CoAR (e.g., ADH6 and AKR1A1) can raise SNO levels and increase protein S-nitrosylation.

In some embodiments, administration of ADH inhibitors, AKR inhibitors, and/or SNO-CoAR inhibitors to a subject can raise SNO levels in the subject, promote protein S-nitrosylation, and treat cardiovascular disorders and diseases, such as congestive heart failure (CHF), cardiac hypertrophy including both atrial and ventricular hypertrophy, myocardial infarction, myocardial ischemia, myocardial ischemia reperfusion injury, cariomyopathies, or arrhythmias.

In some embodiment, the AKR inhibitor is an AKR1A1 inhibitor. In other embodiments, the AKR1A1 inhibitor includes imirestat and analogues thereof.

In some embodiments, the imirestat analogues include compounds selected from the group consisting of:
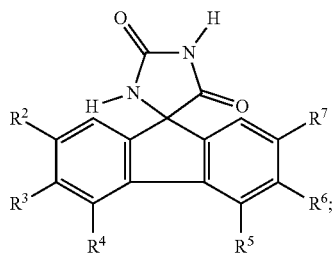
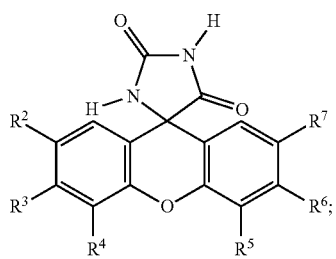
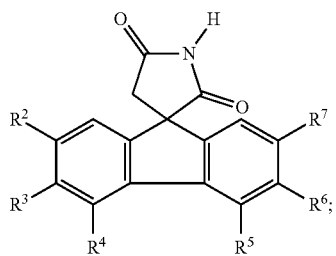
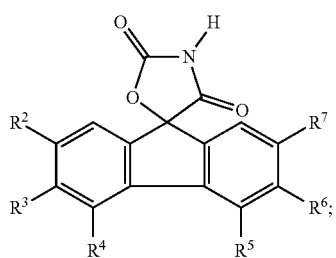
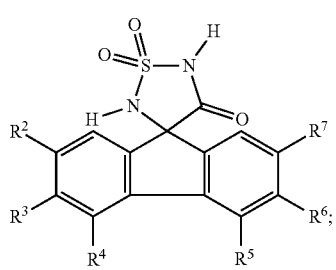
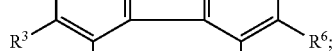
-continued
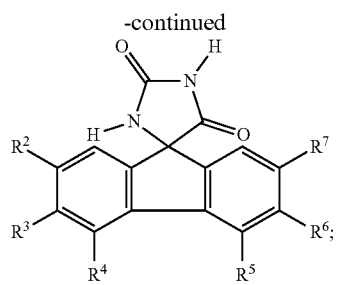
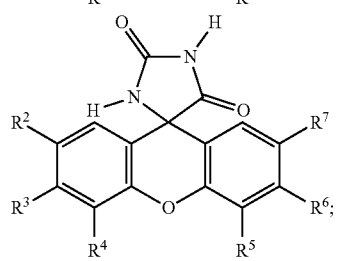
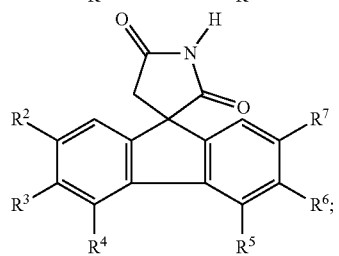
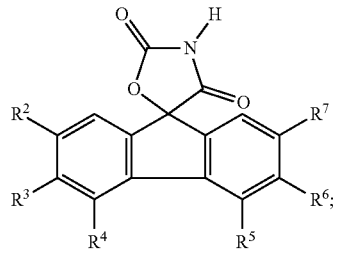
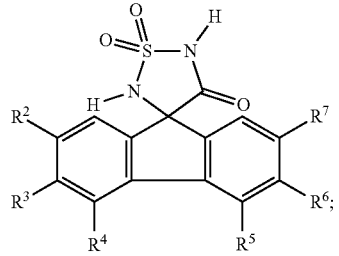
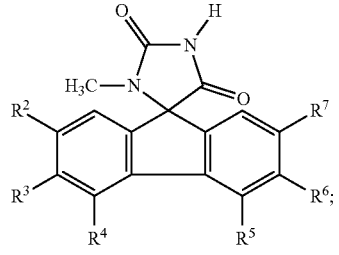
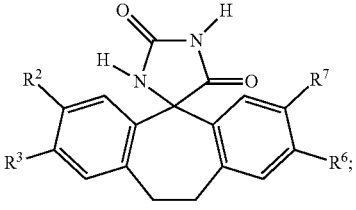

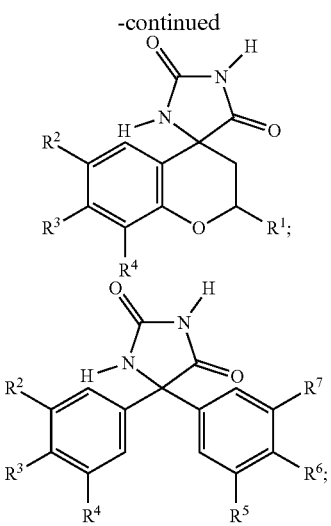

$R^1$, $R^2$, $R^3$, $R^4$, $R^5$, $R^6$, and $R^7$ are the same or different and are independently selected from the group consisting of hydrogen, halogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, heteroaryl or heterocyclyl containing from 5-14 ring atoms, $C_6$-$C_{24}$ alkaryl, $C_6$-$C_{24}$ aralkyl, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ acyloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, carbamido, cyano, amino, $C_1$-$C_{24}$ alkyl amino, $C_5$-$C_{20}$ aryl amino, $C_2$-$C_{24}$ alkylamido, $C_6$-$C_{20}$ arylamido, sulfanamido, imino, alkylimino, arylimino, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, sulfonamide, and combinations thereof; and pharmaceutically acceptable salts thereof.

DETAILED DESCRIPTION

Figure 1A:
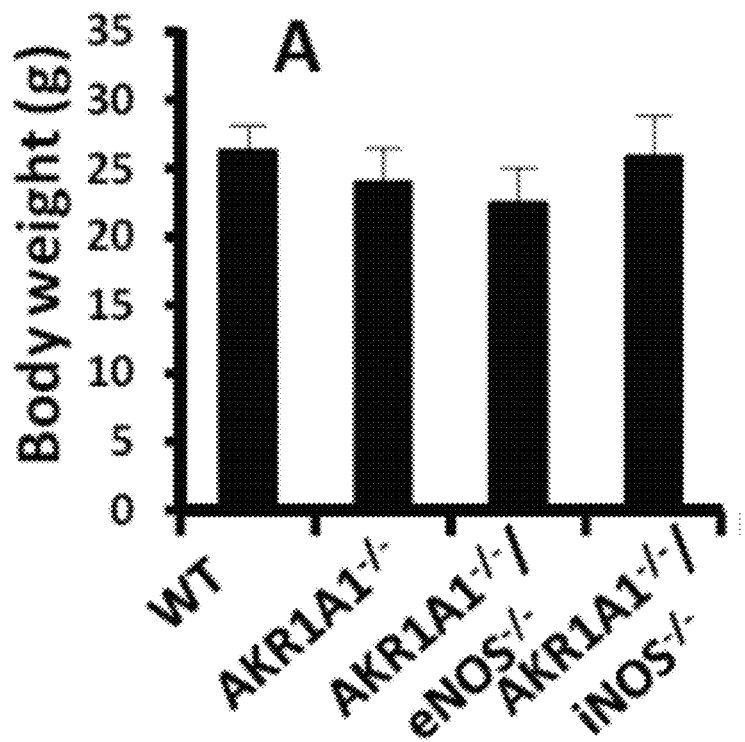
FIG. 1(A-D) illustrate generation and characterization of AKR1A1$^{-/-}$, AKR1A1$^{-/-}$/eNOS$^{-/-}$ and AKR1A1$^{-/-}$/iNOS$^{-/-}$ mice. (A) The body weight of 10-week old WT, AKR1A1$^{-/-}$, AKR1A1$^{-/-}$/eNOS$^{-/-}$ and AKR1A1$^{-/-}$/iNOS$^{-/-}$ mice. (B) Expression of AKR1A1 in hearts of WT and AKR1A1$^{-/-}$ mice. (C) NADPH dependent SNO-CoA reductase activity was measured in heart extracts from WT and AKR1A1$^{-/-}$ mice. (D) Expression of nNOS, iNOS and eNOS in sham-treated or TAC treated hearts.

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis. The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substitutents, e.g., sulfoxides or sulfinamides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n−1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physicochemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardial, intradermal, intraperitoneal, transtracheal, subcutaneous, subcuticular, intra-articular, subcapsular, subarachnoid, intraspinal and intrastemal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively. Prodrugs can also include a precursor (forerunner) of a compound described herein that undergoes chemical conversion by metabolic processes before becoming an active or more active pharmacological agent or active compound described herein.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds, and the like, as well as sulfides that are oxidized to form sulfoxides or sulfones.

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, 3rd ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as H2O, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertable by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analogue" refers to a chemical compound that is structurally similar to another but differs slightly in composition (as in the replacement of one atom by an atom of a different element or in the presence of a particular functional group, or the replacement of one functional group by another functional group). Thus, an analogue is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "IC50," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "substituted alkyls" refers to alkyl moieties having substituents replacing a hydrogen on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). If not otherwise indicated, the terms "alkyl" and "lower alkyl" include linear, branched, cyclic, unsubstituted, substituted, and/or heteroatom-containing alkyl or lower alkyl, respectively.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and alkylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate. The term sulfoxide refers to a sulfur attached to 2 different carbon atoms and one oxygen and the S—O bond can be graphically represented with a double bond (S=O), a single bond without charges (S—O) or a single bond with charges [S(+)-O(−)].

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ acyloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—$NH_2$), carbamido (—NH—(CO)—$NH_2$), cyano (—CN), isocyano (—$N^+C^-$), cyanato (—O—CN), isocyanato (—$ON^+C^-$), isothiocyanato (—S—CN), azido (—N=$N^+$=$N^-$), formyl (—(CO)—H), thioformyl (—(CS)—H), amino (—$NH_2$), mono- and di-($C_1$-$C_{24}$ alkyl)-substituted amino, mono- and di-($C_5$-$C_{20}$ aryl)-substituted amino, $C_2$-$C_{24}$ alkylamido (—NH—(CO)-alkyl), $C_6$-$C_{20}$ arylamido (—NH—(CO)-aryl), imino (—CR=NH where R=hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—$NO_2$), nitroso (—NO), sulfo (—$SO_2$—OH), sulfonato (—$SO_2$—$O^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—$SO_2$-alkyl), $C_5$-$C_{20}$ arylsulfonyl (—$SO_2$-aryl), phosphono (—P(O)($OH$)$_2$), phosphonato (—P(O)($O^-$)$_2$), phosphinato (—P(O)($O^-$)), phospho (—$PO_2$), and phosphino (—$PH_2$); and the hydrocarbyl moieties $C_1$-$C_{24}$ alkyl, $C_2$-$C_{24}$ alkenyl, $C_2$-$C_{24}$ alkynyl, $C_5$-$C_{20}$ aryl, $C_6$-$C_{24}$ alkaryl, and $C_6$-$C_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl.

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

The terms "healthy" and "normal" are used interchangeably herein to refer to a subject or particular cell or tissue that is devoid (at least to the limit of detection) of a disease condition.

Embodiments described herein relate to compositions and methods of modulating protein nitrosylation and particularly relates to the use of alcohol dehydrogenase (ADH) inhibitors (e.g., ADH6 inhibitors), aldoketo reductase (AKR) inhibitors (e.g., AKR1A1 inhibitors), and/or SNO-Coenzyme A reductase (SNO-CoAR) inhibitors (e.g., ADH6 inhibitors and AKR1A1 inhibitors) to increase or enhance protein S-nitrosylation in the heart of a subject and treat cardiovascular disorders and diseases, such as congestive heart failure (CHF), cardiac hypertrophy including both atrial and ventricular hypertrophy, myocardial infarction, myocardial ischemia, myocardial ischemia reperfusion injury, cardiomyopathies, or arrhythmias.

AKR1A1 is a mammalian SNO-CoA reductase, which specifically and efficiently reduces SNO-CoA to CoA by using reducing equivalents of NADPH. AKR1A1 was also found to metabolize GSNO, a known nitrosylating agent. Knockout of AKR1A1 in mice was found to increase cellular protein S-nitrosylation, reduce oxidative stress, and provide cardioprotection against myocardial ischemia reperfusion injury. Inhibition of ADHs (e.g., ADH6), AKRs (e.g., AKR1A1), and/or SNO-CoAR (e.g., ADH6 and AKR1A1) can raise SNO levels and increase protein S-nitrosylation.

In some embodiments, the AKR inhibitor administered to a subject can be a partially selective AKR1A1 inhibitor and/or partially selective AKR1B1 inhibitor. For example, the AKR inhibitor can inhibit both AKR1A1 and AKR1B1, inhibit AKR1B1 at a lower $IC_{50}$ than AKR1A1, or inhibit AKR1A1 at a lower $IC_{50}$ than AKR1B1. Optionally, a selective or partially selective AKR1A1 inhibitor can be administered in combination with a selective or partially selective AKR1B1 inhibitor.

In some embodiments, the AKR1A1 inhibitor can have an $IC_{50} \leq 5$ µM, $\leq 1$ µM, or $\leq 100$ nM. In other embodiments, the AKR1A1 inhibitor can have a selectivity for AKR1A1 versus AKR1B1 $\geq 2$ times, $\geq 5$ times, $\geq 10$ times, $\geq 20$ times, $\geq 30$ times, $\geq 40$ times, $\geq 50$ times or more times. In other embodiments, the AKR1A1 inhibitor can have a selectivity for AKR1A1 versus other AKRs $\geq 2$ times, $\geq 5$ times, $\geq 10$ times, $\geq 20$ times, $\geq 30$ times, $\geq 40$ times, $\geq 50$ times or more times. In still other embodiments, the AKR1A1 inhibitor can have an AKR1A1 $IC_{50} \leq 400$ nM, $\leq 300$ nM, $\leq 200$ nM, $\leq 100$ nM, $\leq 50$ nM, or $\leq 25$ nM and a combined AKR1B1 and AKR1A1 $IC_{50} \leq 500$ nM, $\leq 400$ nM, $\leq 300$ nM, $\leq 200$ nM (e.g., less than 100 nM).

In some embodiments, the selectivity of the AKR inhibitor for AKR1A1 inhibition versus other AKRs, such as AKR1B1, can be measured using S-nitroso-Coenzyme A (SNO-CoA) as a substrate. In this instance where SNO-CoA is used as a substrate to measure AKR activity, the AKR inhibitor can have a selectivity for AKR1A1 versus AKR1B1 of $\geq 2$ times, $\geq 5$ times, $\geq 10$ times, $\geq 20$ times, $\geq 30$ times, $\geq 40$ times, $\geq 50$ times or more. In some embodiments, the AKR inhibitor can have negligible inhibition of AKR1B1 activity of SNO-CoA, and particularly compared to AKR1A1 activity.

In other embodiments, the AKR1B1 inhibitor can have an $IC_{50} \leq 5$ µM, $\leq 1$ µM, or $\leq 100$ nM. In other embodiments, the AKR1B1 inhibitor can have a selectivity for AKR1B1 versus AKR1A1 $\geq 2$ times, $\geq 5$ times, $\geq 10$ times, $\geq 20$ times, $\geq 30$ times, $\geq 40$ times, $\geq 50$ times or more times. In other embodiments, the AKR1B1 inhibitor can have a selectivity for AKR1B1 versus other AKRs $\geq 50$ times. In still other embodiments, the AKR1B1 inhibitor can have an AKR1B1 $IC_{50} \leq 300$ nM, $\leq 200$ nM, $\leq 100$ nM, $\leq 50$ nM, or $\leq 25$ nM and a combined AKR1B1 and AKR1A1 $IC_{50} \leq 500$ nM, $\leq 400$ nM, $\leq 300$ nM, $\leq 200$ nM (e.g., less than 100 nM).

Examples of selective and partially selective AKR1A1 inhibitors, including partially selective inhibitors of AKR1A1 activity of SNO-CoA, can include Imirestat (2,7-Difluoro-2'H,5'H-spiro[fluorene-9,4'-imidazolidine]-2',5'-dione) and analogues thereof. Other examples of selective and partially selective AKR1A1 inhibitors can include Tolrestat, Oxo-Tolrestat, Epalrestat, Fidarestat, Statil, Sorbinil, Ranirestat, and Minalrestat.

In some embodiments, the imirestat analogues can include compounds selected from the group consisting of:

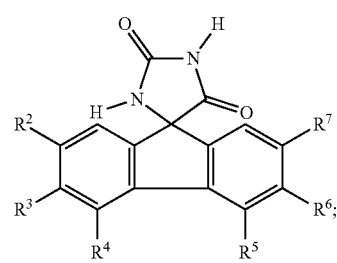

-continued
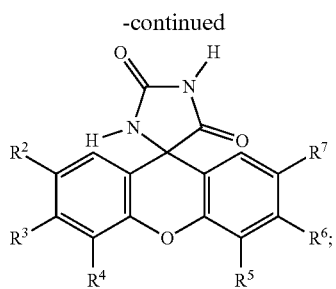
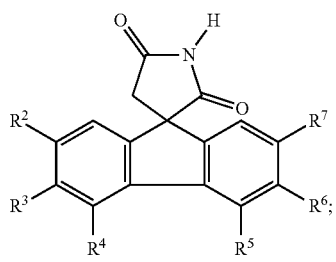
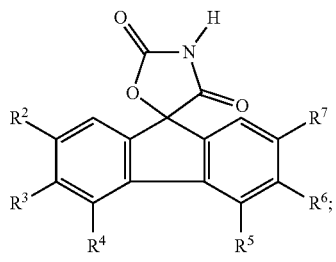
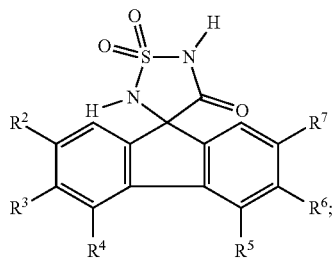
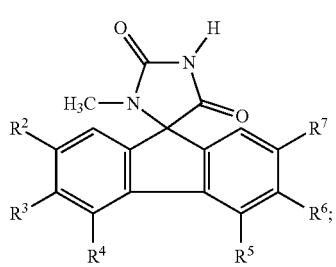
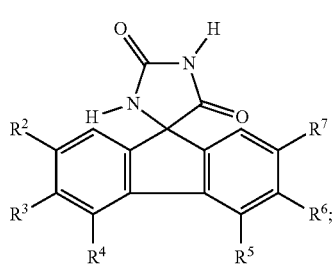
-continued
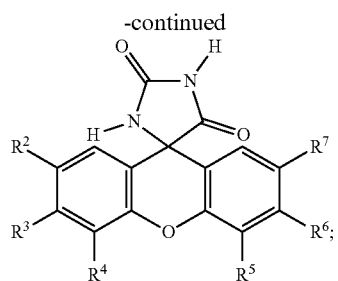
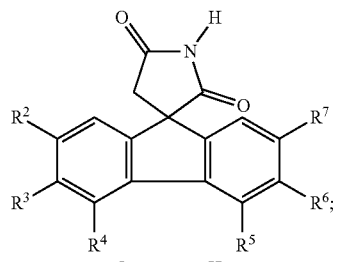
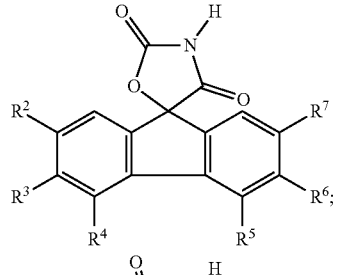
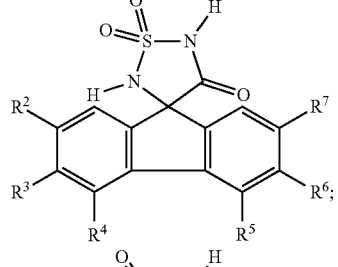
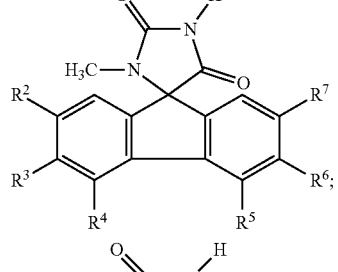
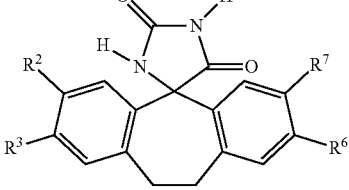
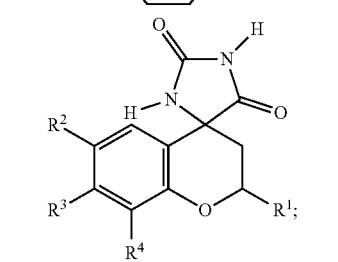

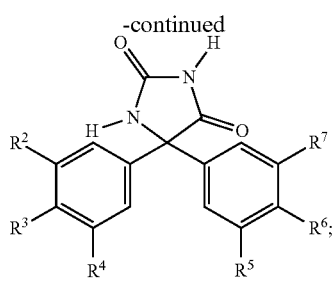

wherein $R^1$, $R^2$, $R^3$, $R^4$, $R^5$, $R^6$, and $R^7$ are the same or different and are independently selected from the group consisting of hydrogen, halogen, substituted or unsubstituted $C_1$-$C_{24}$ alkyl, $C_2$-$C_{24}$ alkenyl, $C_2$-$C_{24}$ alkynyl, $C_3$-$C_{20}$ aryl, heterocycloalkenyl containing from 5-6 ring atoms, (wherein from 1-3 of the ring atoms is independently selected from N, NH, N($C_1$-$C_6$ alkyl), NC(O)($C_1$-$C_6$ alkyl), O, and S), heteroaryl or heterocyclyl containing from 5-14 ring atoms, (wherein from 1-6 of the ring atoms is independently selected from N, NH, N($C_1$-$C_3$ alkyl), O, and S), $C_6$-$C_{24}$ alkaryl, $C_6$-$C_{24}$ aralkyl, halo, silyl, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ acyloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO$^-$), carbamoyl (—(CO)—NH$_2$), $C_1$-$C_{24}$ alkylcarbamoyl (—(CO)—NH($C_1$-$C_{24}$ alkyl)), arylcarbamoyl (—(CO)—NH-aryl), carbamido (—NH—(CO)—NH$_2$), cyano(—CN), amino (—NH$_2$), $C_1$-$C_{24}$ alkyl amino, $C_5$-$C_{20}$ aryl amino, $C_2$-$C_{24}$ alkylamido (—NH—(CO)-alkyl), $C_6$-$C_{20}$ arylamido (—NH—(CO)-aryl), sulfanamido (—SO$_2$NR$_2$ where R is independently H, alkyl, aryl or heteroaryl), imino (—CR=NH where R is hydrogen, $C_1$-$C_{24}$ alkyl, $C_5$-$C_{20}$ aryl, $C_6$-$C_{24}$ alkaryl, $C_6$-$C_{24}$ aralkyl, etc.), alkylimino (—CR=N(alkyl), where R=hydrogen, alkyl, aryl, alkaryl, aralkyl, etc.), arylimino (—CR=N (aryl), where R=hydrogen, alkyl, aryl, alkaryl, etc.), sulfo (—SO$_2$—OH), sulfonato (—SO$_2$—O$^-$), $C_1$-$C_{24}$ alkylsulfanyl (—S-alkyl; also termed "alkylthio"), arylsulfanyl (—S-aryl; also termed "arylthio"), $C_1$-$C_{24}$ alkylsulfinyl (—(SO)-alkyl), $C_5$-$C_{20}$ arylsulfinyl (—(SO)-aryl), $C_1$-$C_{24}$ alkylsulfonyl (—SO$_2$-alkyl), $C_5$-$C_{20}$ arylsulfonyl (—SO$_2$-aryl), sulfonamide, and combinations thereof; and pharmaceutically acceptable salts thereof.

In other embodiments, $R^1$, $R^2$, $R^3$, $R^4$, $R^5$, $R^6$, and $R^7$ are the same or different and are independently selected from the group consisting of hydrogen, halogen, alkyl, haloalkyl, cycloalkyl, heterocyclyl, heteroaryl, —OH, carboxyl, alkylene carboxyl, alkylene cycloalkyl, alkylene heterocyclyl, alkylene heteroaryl, alkylene-C(O)N($R^8$)$_m$, —O-alkylene-carboxyl, —O-arylene-carboxyl, —O-alkylene-arylene, —O-alkylene-heteroaryl, —O-alkylene-heterocyclyl, carboxyl, alkyne carboxyl, —O-alkylene-N($R^8$)$_2$, —N($R^8$)$_2$, —N($R^8$)(alkylene-OH), —C(O)N($R^8$)$_m$, —C(O)N($R^8$)(alkylene-OH), —C(O)N($R^8$)(alkylene carboxyl), —C(O)N($R^8$)S(O)$_m$-alkyl, —C(O)-alkyl, —C(O)O-alkyl, alkoxy, or —S(O)$_m$-alkyl;

each $R^8$ is independently, H, alkyl, -alkylene-OH optionally substituted with —OH, -alkylene-NH$_2$, -alkylene-N($R^9$)$_2$, -alkylene-O-alkylene-OH, -alkylene-O-alkylene-NH$_2$, —C(O)-alkyl, —C(O)O-alkyl, -alkylene-COOH, or —S(O)$_m$-alkyl;

or alternatively, two $R^8$ together with the N atom to which they are attached can form a 4- to 7-membered heterocycle, optionally containing an additional heteroatom selected from O, S, or N, and wherein the heterocycle is optionally substituted with $R^9$; and $R^9$ is halogen, alkyl, or alkoxy, m is 0, 1, or 2; and pharmaceutically acceptable salts thereof.

In other embodiments, the imirestat analogues can include compounds selected from the group consisting of:

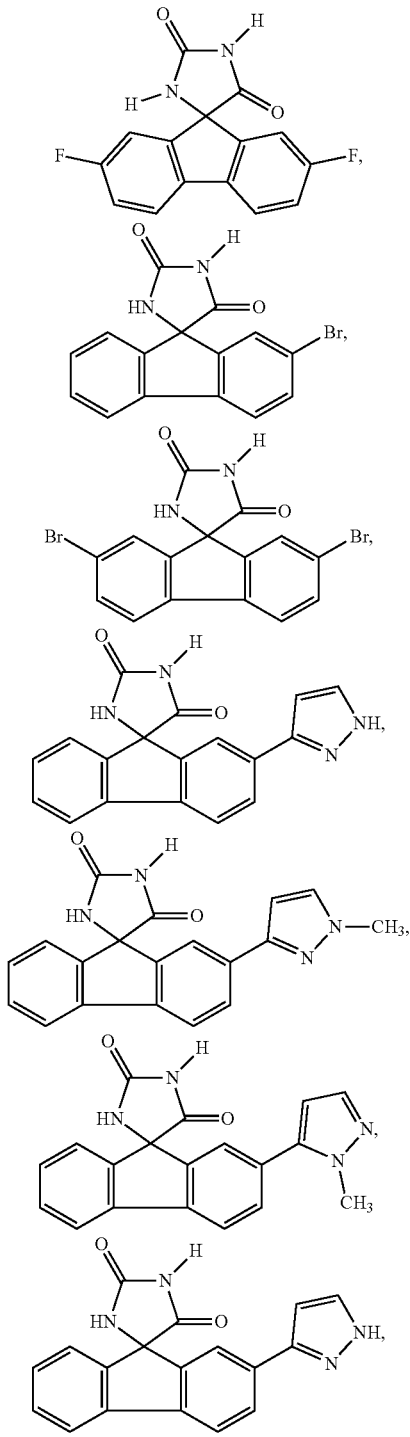

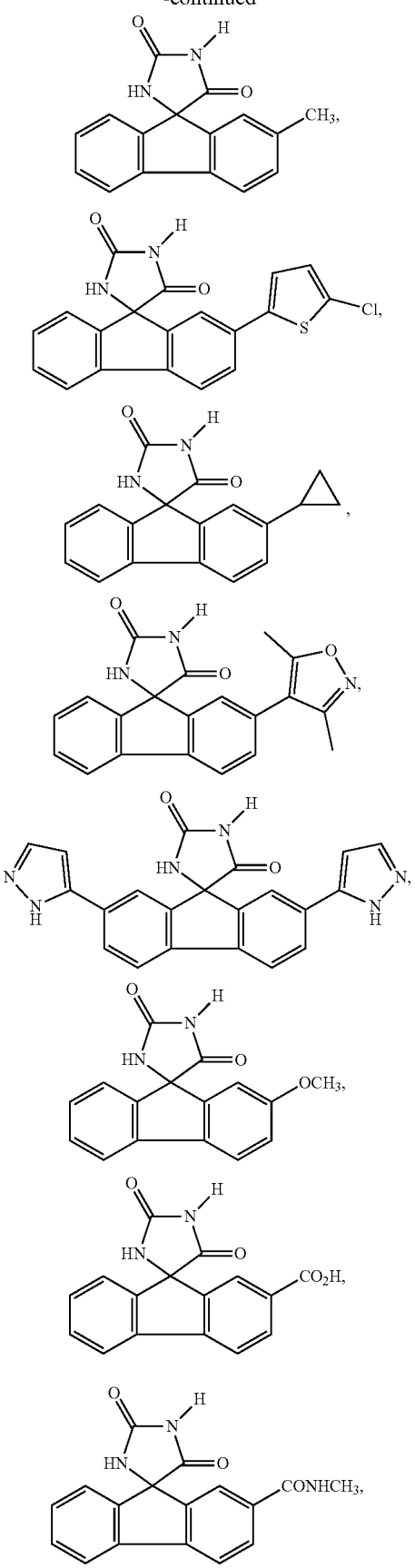
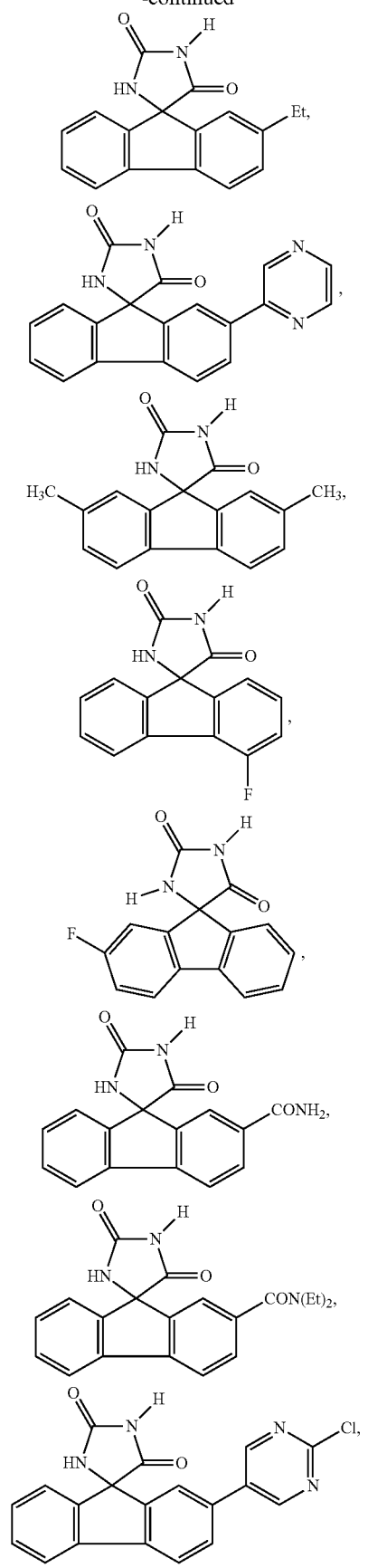

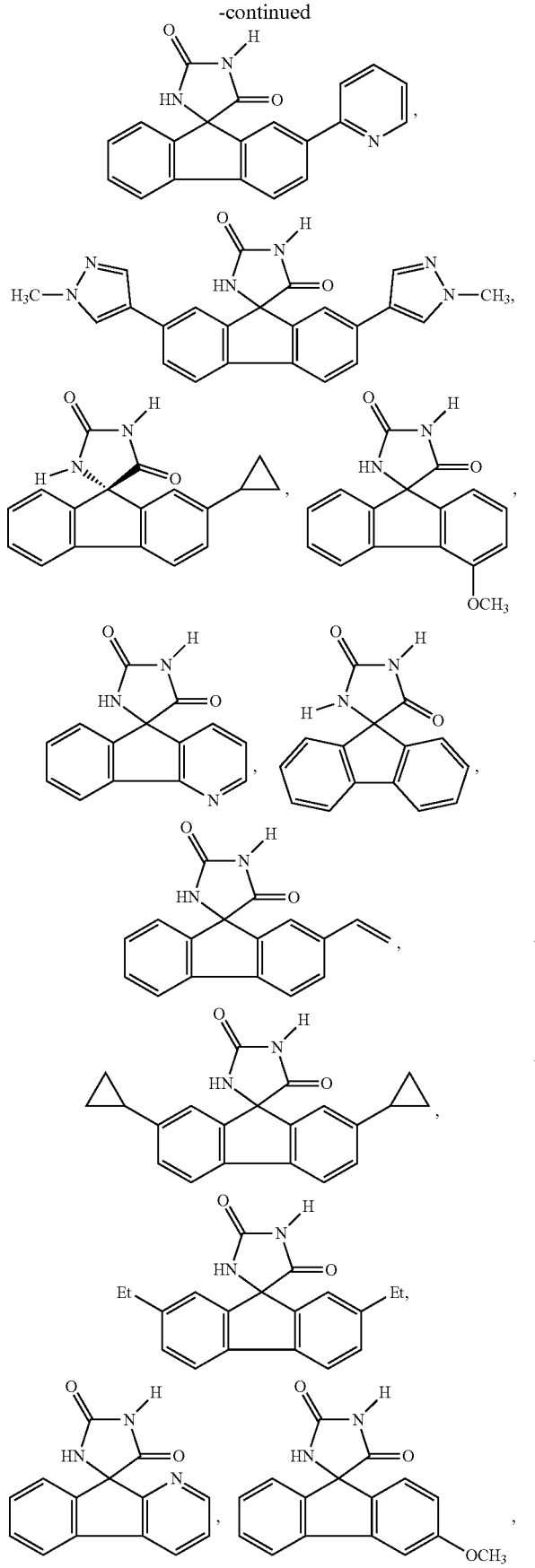
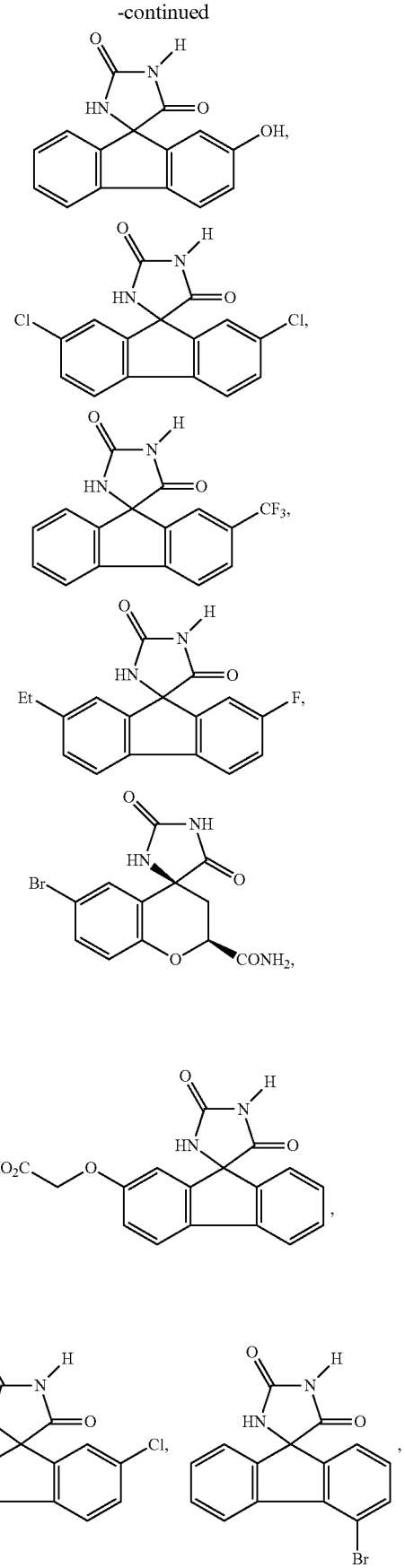

-continued
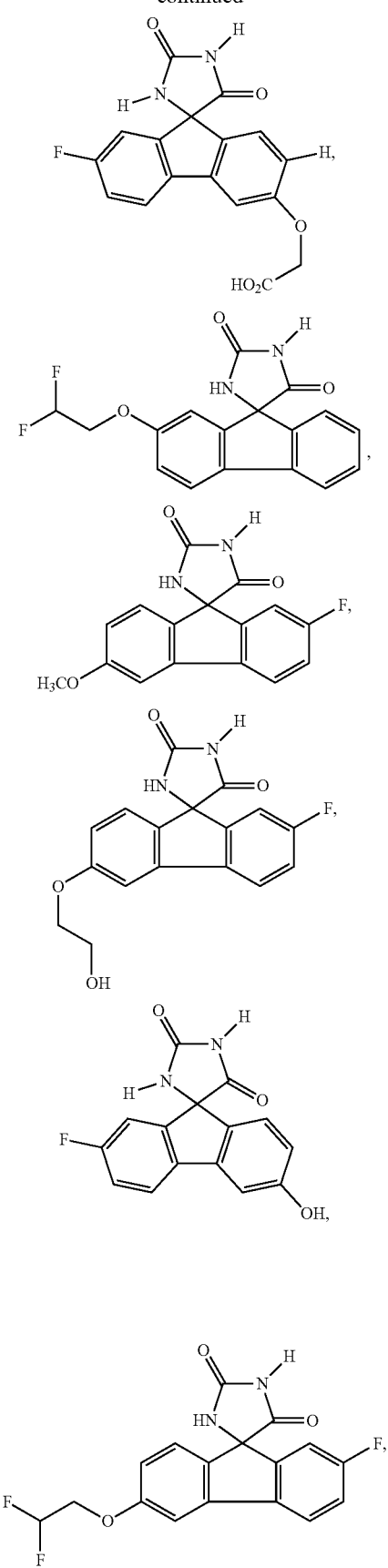
-continued
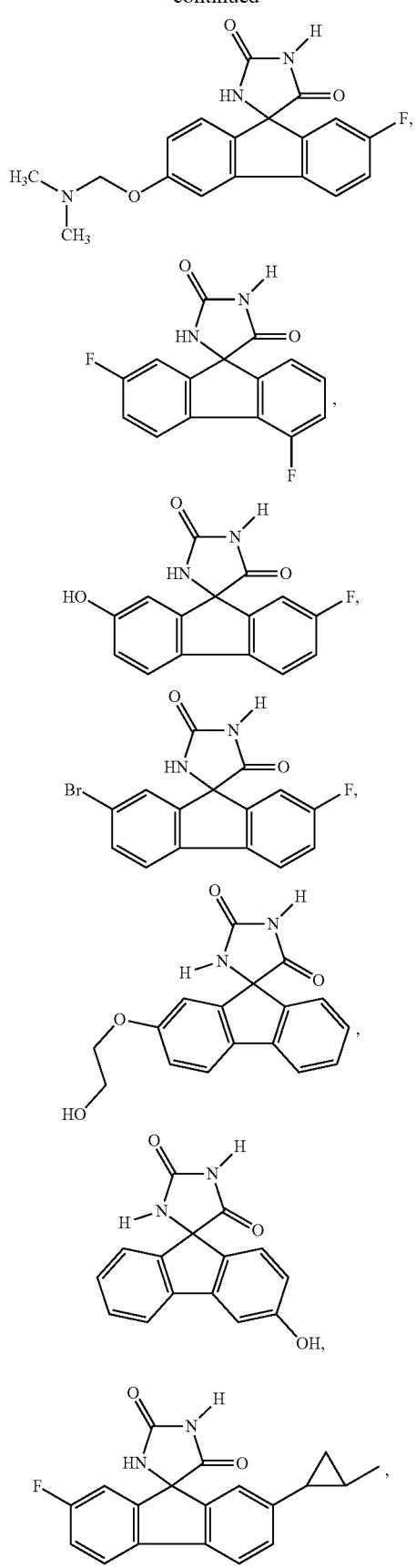

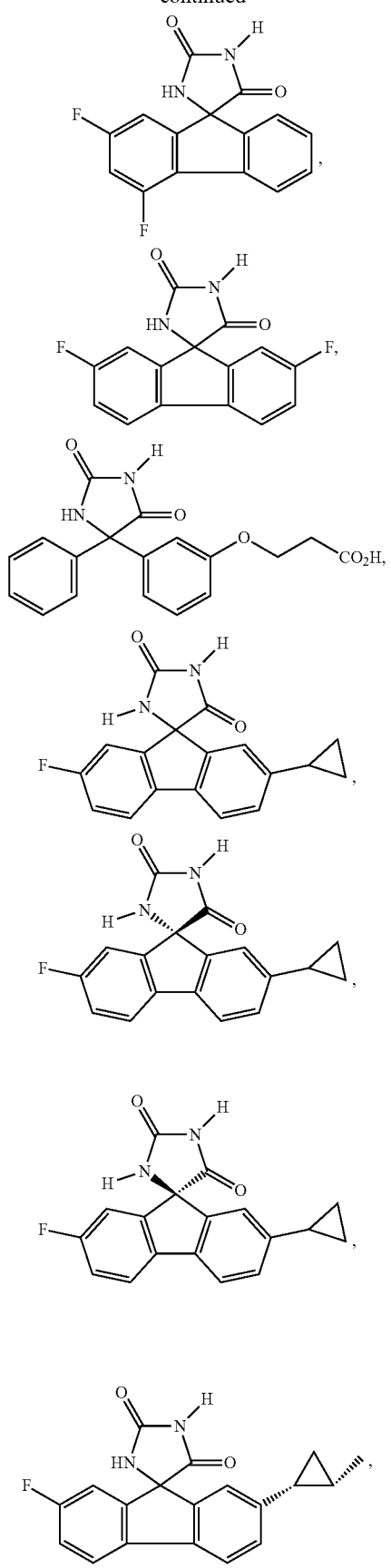
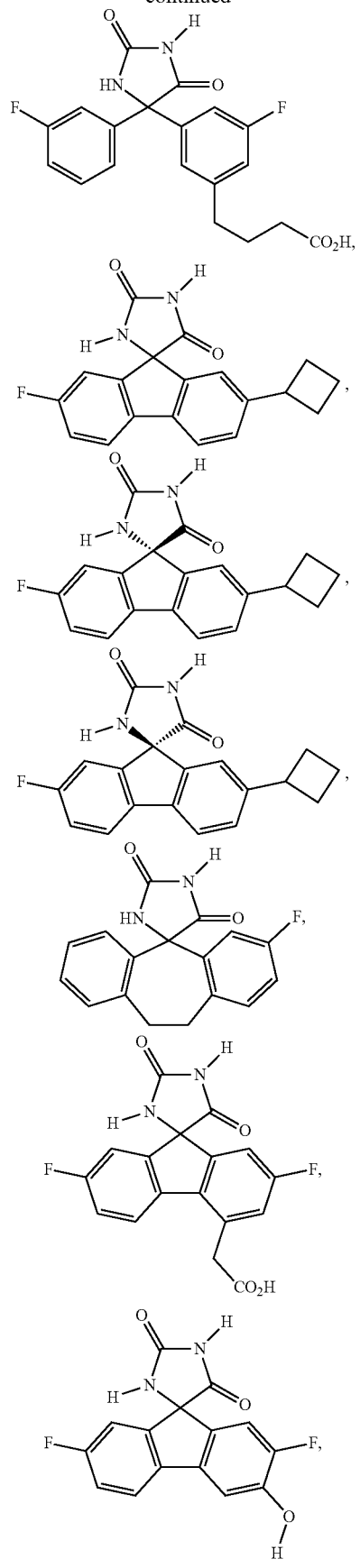

-continued
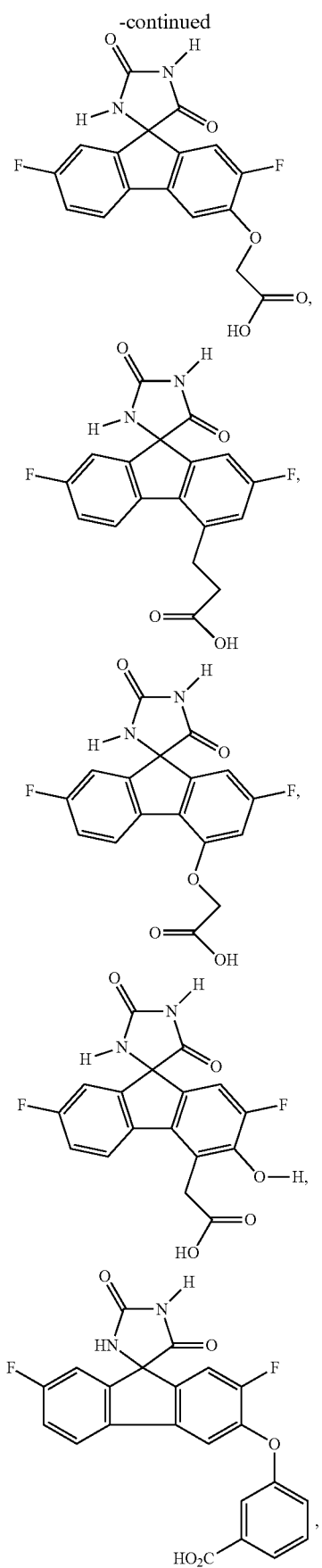
-continued
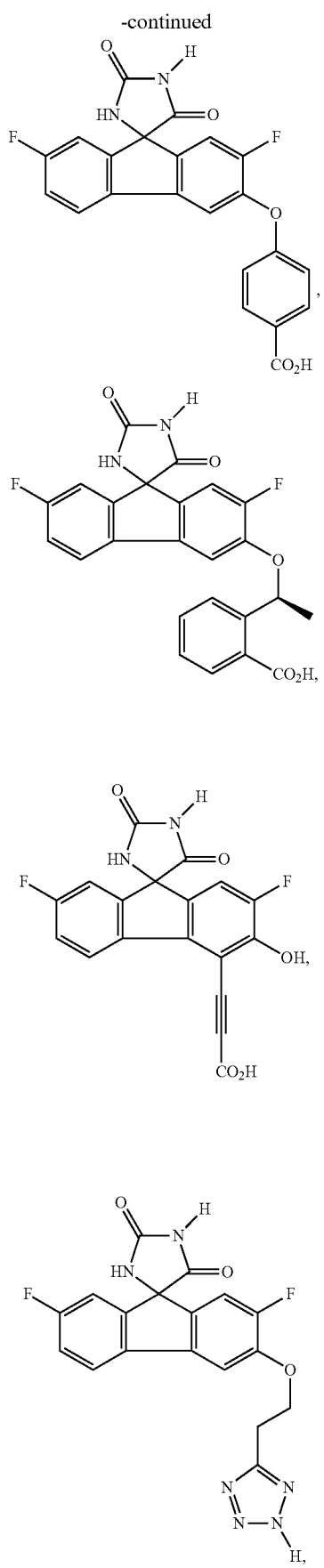

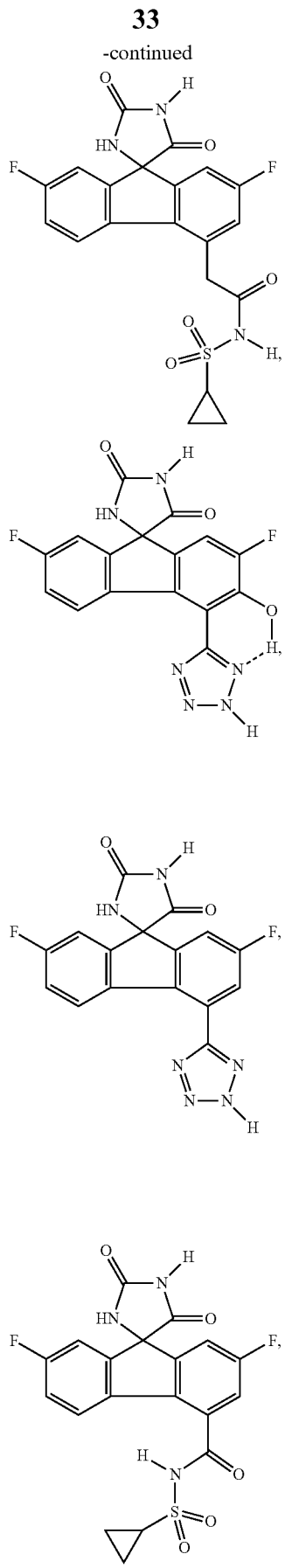
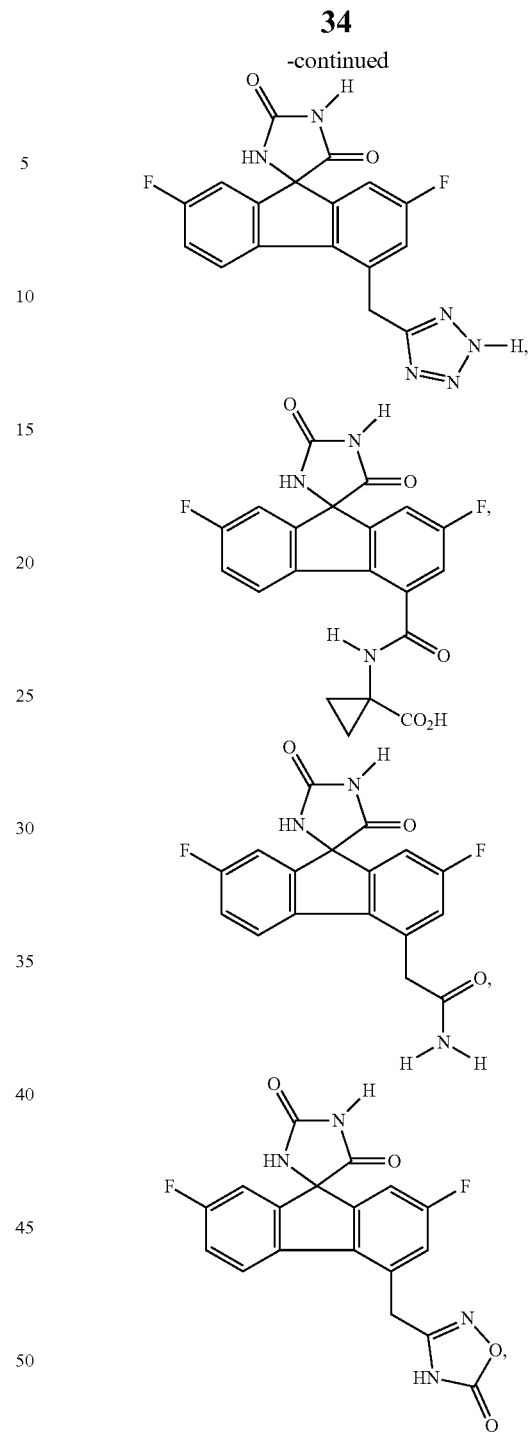

and pharmaceutically acceptable salts thereof.

Still other examples of selective and/or partially selective AKR1A1 inhibitor are disclosed in the following publications: Mechanism of Human Aldehyde Reductase: Characterization of the Active Site Pocket, Oleg A. Barski et al., Biochemistry 1995, 34, 11264-11275, In vivo role of aldehyde reductase, M. Takahashi et al., Biochim Biophys Acta. 2012 November; 1820(11):1787-96, The Aldo-Keto Reductase Superfamily and its Role in Drug Metabolism and Detoxification, Oleg A. Barski et al., Drug Metab Rev. 2008; 40(4): 553-624, Asborin Inhibits Aldo/Keto Reductase 1A1, Matthias Scholz et al., ChemMedChem, 2011, 6, 89-93, Inhibition of Aldehyde Reductase by Aldose Reductase Inhibitors, Sanai Sato et al., Biochemical Pharmacology, 1990. 40, 1033-1042, Inhibition of human aldose and aldehyde reductases by non-steroidal anti-inflammatory drugs, D. Michelle Ratliff et al., Advances in Experimental Medicine and Biology, Volume: 463, Issue: Enzymology and Molecular Biology of Carbonyl Metabolism 7, Pages: 493-499 (1999.), Inhibition of aldehyde reductases, Philip J. Schofield et al., Progress in Clinical and Biological Research, 1987, 232, Issue: Enzymol. Mol. Biol. Carbonyl Metab., 287-96, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in Vitro Activity, Polyxeni Alexiou et al., J. Med. Chem. 2010, 53, 7756-7766, Aldose Reductase Inhibitors as Potential Therapeutic Drugs of Diabetic Complications, By Changjin Zhu, DOI: 10.5772/54642, Aldose Reductase Inhibitors: A Potential New Class of Agents for the Pharmacological Control of Certain Diabetic Complications, Peter F. Kador et al., Journal of Medicinal Chemistry, 1985, 28, 841-849, Recent clinical experience with aldose reductase inhibitors, H. M. J. Krans, Journal of Diabetes and its Complications, 1992, 6, 39-44, A Novel Series of Non-Carboxylic Acid, Non-Hydantoin Inhibitors of Aldose Reductase with Potent Oral Activity in Diabetic Rat Models: 6-(5-Chloro-3-methylbenzofuran-2-sulfonyl)-2H-pyridazin-3-one and Congeners, Banavara L. Mylari et al., J. Med. Chem. 2005, 48, 6326-6339, A Diverse Series of Substituted Benzenesulfonamides as Aldose Reductase Inhibitors with Antioxidant Activity: Design, Synthesis, and in Vitro Activity, Polyxeni Alexiou et al., J. Med. Chem. 2010, 53, 7756-7766, all of which are incorporated herein by reference in their entirety. It will be appreciated that any potential selective or partially selective AKR1A1 inhibitors can be used in the compositions and methods recited herein.

The ADH inhibitor can be include auramine O, allicin, 1,5-anilinonaphthalenesulfonic acid, 1,7-anilinonaphthalenesulfonic acid, 1,8-anilinonaphthalenesulfonic acid, berberine, canavanine, 2,2'-diprypyl, imidazole, m-methylbenzamide, 4-methylpyrazole, pyrazole, 4-pentylpyrazole, O-phenanthroline, alrestatin, anthranic acid, O-carboxybenzaldehyde, 2,3-dimethylsuccinic acid, ethacrynic acid, isonicotinic acid, phenacemide, quercetin, quercitrin, sorbinil, tetramethyleneglutaric acid, valproic acid, propranolol, 2,2, 2-trichloroethanol, 4,5-diaminopyrazole and its derivatives and 2-ethyl-5-methyl-2H-3,4-diaminopyrazole. See U.S. Patent Application Publication 20030138390, which is incorporated herein by reference in its entirety.

Fomepizole (4-methylpyrazole) is also a competitive inhibitor of ADH. Pyrazole and its 4-substituted derivatives competitively inhibit the binding of alcohol substrates through the formation of a tight enzyme. $NAD^+$.inhibitor complex, in which pyrazole nitrogens interact with both zinc and $NAD^+$. Xie et al., J. Biol. Chem., 272:18558-18563 (1997), herein incorporated by reference.

CNAD (5-beta-D-ribofuranosylnicotinamide adenine dinucleotide) is an isomeric and isomeric analogue of NAD, in which the nicotinamide ring is linked to the sugar via a C-glycosyl (C5-C1') bond. CNAD acts as a general dehydrogenase inhibitor but shows unusual specificity and affinity for liver alcohol dehydrogenase. Goldstein et al., J. Med. Chem., 37:392-9 (1994), herein incorporated by reference.

Other ADH inhibitors include dimethyl sulfoxide, Perlman and Wolff, Science, 160:317-9 (1968); and p-methylbenzyl hydroperoxide, Skursky et al., Biochem Int., 26:899-904 (1992), herein incorporated by reference.

In some embodiments, the ADH inhibitor can be a selective ADH6 inhibitor or partially selective ADH6 inhibitor that does not inhibit ADH3. In other embodiments, the ADH inhibitor does not inhibit ADH3 but inhibits other ADHs, such as ADH6.

In other embodiments, the ADH inhibitor and/or AKR inhibitor can include an agent that reduces or inhibits ADH and/or AKR expression, such as ADH6 expression or AKR1A1 expression, in tissue or cells of a subject in need thereof. "Expression", means the overall flow of information from a gene to produce a gene product (typically a protein, optionally post-translationally modified or a functional/structural RNA).

In some embodiments, the agent can include an RNAi construct that inhibits or reduces expression of the ADH and/or AKR expression in a cell. RNAi constructs comprise double stranded RNA that can specifically block expression of a target gene. "RNA interference" or "RNAi" is a term initially applied to a phenomenon observed in plants and worms where double-stranded RNA (dsRNA) blocks gene expression in a specific and post-transcriptional manner.

As used herein, the term "dsRNA" refers to siRNA molecules or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species, which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences.

The choice of promoter and other regulatory elements generally varies according to the intended host cell. In general, expression vectors of utility in recombinant DNA techniques are often in the form of "plasmids" which refer to circular double stranded DNA loops, which, in their vector form are not bound to the chromosome. In the present specification, "plasmid" and "vector" are used interchangeably as the plasmid is the most commonly used form of vector. However, the application describes other forms of expression vectors that serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, embodiments tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript.

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA Likewise, bases may be modified to block the activity of adenosine deaminase. The RNAi construct may be produced enzymatically or by partial/total organic synthesis, a modified ribonucleotide can be introduced by in vitro enzymatic or organic synthesis.

Methods of chemically modifying RNA molecules can be adapted for modifying RNAi constructs (see for example, *Nucleic Acids Res*, 25:776-780; *J Mol Recog* 7:89-98; *Nucleic Acids Res* 23:2661-2668; *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodie-sters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount, which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules described herein can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (*Proc Natl Acad Sci USA*, 98:9742-9747; *EMBO J*, 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain embodiments, the RNAi construct is in the form of a hairpin structure (named as hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, *Genes Dev,* 2002, 16:948-58; Nature, 2002, 418:38-9; RNA, 2002, 8:842-50; and *Proc Natl Acad Sci,* 2002, 99:6047-52. Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an example of a vector for bi-directional transcription of a transgene to yield both sense and antisense RNA transcripts of the same transgene in a eukaryotic cell. Accordingly, certain embodiments provide a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell.

In some embodiments, a lentiviral vector can be used for the long-term expression of a siRNA, such as a short-hairpin RNA (shRNA), to knockdown expression of the RPTP in a cancer cell. Although there have been some safety concerns about the use of lentiviral vectors for gene therapy, self-inactivating lentiviral vectors are considered good candidates for gene therapy as they readily transfect mammalian cells.

By way of example, short-hairpin RNA (shRNA) down regulation of the AKR1A1 expression can be created using OligoEngene software (OligoEngine, Seattle, Wash.) to identify sequences as targets of siRNA. The oligo sequences can be annealed and ligated into linearized pSUPER RNAi vector (OligoEngine, Seattle, Wash.) and transformed in *E coli* strain DH5α cells. After positive clones are selected, plasmid can be transfected into 293T cells by calcium precipitation. The viral supernatant collected containing shRNA can then be used to infect mammalian cells in order to down regulate the AKR1A1.

AKR1A1 siRNA, shRNA plasmids, and shRNA lentiviral particle gene silencers are commercially available from Santa Cruz Biotechnology under the product names sc-78566, sc-78566-SH, and sc-78566-V.

In another embodiment, the ADH and/or AKR inhibitor can include antisense oligonucleotides. Antisense oligonucleotides are relatively short nucleic acids that are complementary (or antisense) to the coding strand (sense strand) of the mRNA encoding a particular protein. Although antisense oligonucleotides are typically RNA based, they can also be DNA based. Additionally, antisense oligonucleotides are often modified to increase their stability.

The binding of these relatively short oligonucleotides to the mRNA is believed to induce stretches of double stranded RNA that trigger degradation of the messages by endogenous RNAses. Additionally, sometimes the oligonucleotides are specifically designed to bind near the promoter of the message, and under these circumstances, the antisense oligonucleotides may additionally interfere with translation of the message. Regardless of the specific mechanism by which antisense oligonucleotides function, their administration to a cell or tissue allows the degradation of the mRNA encoding a specific protein. Accordingly, antisense oligonucleotides decrease the expression and/or activity of a particular protein (e.g., AKR1A1).

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups, such as peptides (e.g., for targeting host cell receptors), or agents facilitating transport across the cell membrane (see, e.g., *Proc Natl Acad Sci* 86:6553-6556; *Proc Natl Acad Sci* 84:648-652; PCT Publication No. WO88/09810, published Dec. 15, 1988) or the blood-brain barrier (see, e.g., PCT Publication No. WO89/10134, published Apr. 25, 1988), hybridization-triggered cleavage agents (See, e.g., *BioTechniques* 6:958-976) or intercalating agents. (See, e.g., *Pharm Res* 5:539-549). To this end, the oligonucleotide may be conjugated or coupled to another molecule.

Oligonucleotides described herein may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein et al. (*Nucl. Acids Res.* 16:3209), methylphosphonate oligonucleotides can be prepared by use of controlled pore glass polymer supports (*Proc Natl Acad Sci* 85:7448-7451).

The selection of an appropriate oligonucleotide can be performed by one of skill in the art. Given the nucleic acid sequence encoding a particular protein, one of skill in the art can design antisense oligonucleotides that bind to that protein, and test these oligonucleotides in an in vitro or in vivo system to confirm that they bind to and mediate the degradation of the mRNA encoding the particular protein. To design an antisense oligonucleotide that specifically binds to and mediates the degradation of a particular protein, it is important that the sequence recognized by the oligonucleotide is unique or substantially unique to that particular protein. For example, sequences that are frequently repeated across protein may not be an ideal choice for the design of an oligonucleotide that specifically recognizes and degrades a particular message. One of skill in the art can design an oligonucleotide, and compare the sequence of that oligonucleotide to nucleic acid sequences that are deposited in publicly available databases to confirm that the sequence is specific or substantially specific for a particular protein.

A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systematically.

However, it may be difficult to achieve intracellular concentrations of the antisense oligonucleotide sufficient to suppress translation on endogenous mRNAs in certain instances. Therefore, another approach utilizes a recombinant DNA construct in which the antisense oligonucleotide is placed under the control of a strong pol III or pol II promoter. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells.

Expression of the sequence encoding the antisense RNA can be by a promoter known in the art to act in mammalian, preferably human cells. Such promoters can be inducible or constitutive. Such promoters include but are not limited to: the SV40 early promoter region (*Nature* 290:304-310), the promoter contained in the 3' long terminal repeat of Rous sarcoma virus (*Cell* 22:787-797), the herpes thymidine kinase promoter (*Proc Natl Acad Sci* 78:1441-1445), the regulatory sequences of the metallothionein gene (*Nature* 296:39-42), etc. A type of plasmid, cosmid, YAC or viral vector can be used to prepare the recombinant DNA construct that can be introduced directly into the tissue site. Alternatively, viral vectors can be used which selectively infect the desired tissue, in which case administration may be accomplished by another route (e.g., systematically).

The ADH inhibitors, AKR inhibitors, and/or SNO-CoAR inhibitors can be provided in pharmaceutical compositions with at least one pharmaceutically acceptable carrier. Suitable carriers are described in "Remington: The Science and Practice, Twentieth Edition," published by Lippincott Williams & Wilkins, which is incorporated herein by reference. Pharmaceutical compositions according to the invention may also comprise one or more non-inventive compound active agents.

The compositions comprising ADH inhibitors, AKR inhibitors, and/or SNO-CoAR inhibitors can be utilized in any pharmaceutically acceptable dosage form, including, but not limited to injectable dosage forms, liquid dispersions, gels, aerosols, ointments, creams, lyophilized formulations, dry powders, tablets, capsules, controlled release formulations, fast melt formulations, delayed release formulations, extended release formulations, pulsatile release formulations, mixed immediate release and controlled release formulations, etc. Specifically, the ADH inhibitors, AKR inhibitors, and/or SNO-CoAR inhibitors can be formulated: (a) for administration selected from the group consisting of oral, pulmonary, intravenous, intra-arterial, intrathecal, intra-articular, rectal, ophthalmic, colonic, parenteral, intracisternal, intravaginal, intraperitoneal, local, buccal, nasal, and topical administration; (b) into a dosage form selected from the group consisting of liquid dispersions, gels, aerosols, ointments, creams, tablets, sachets, and capsules; (c) into a dosage form selected from the group consisting of lyophilized formulations, dry powders, fast melt formulations, controlled release formulations, delayed release formulations, extended release formulations, pulsatile release formulations, and mixed immediate release and controlled release formulations; or (d) any combination thereof.

Solutions or suspensions used for parenteral, intradermal, or subcutaneous application can comprise one or more of the following components: (1) a sterile diluents, such as water for injection, saline solution, fixed oils, polyethylene glycols, glycerine, propylene glycol, or other synthetic solvents; (2) antibacterial agents, such as benzyl alcohol or methyl parabens; (3) antioxidants, such as ascorbic acid or sodium bisulfite; (4) chelating agents, such as ethylenediaminetetraacetic acid; (5) buffers, such as acetates, citrates, or phosphates; and (5) agents for the adjustment of tonicity, such as sodium chloride or dextrose. The pH can be adjusted with acids or bases, such as hydrochloric acid or sodium hydroxide. A parenteral preparation can be enclosed in ampoules, disposable syringes, or multiple dose vials made of glass or plastic.

Pharmaceutical compositions suitable for injectable use may comprise sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.), or phosphate buffered saline (PBS). In all cases, the composition must be sterile and should be fluid to the extent that easy syringability exists. The pharmaceutical composition should be stable under the conditions of manufacture and storage and should be preserved against the contaminating action of microorganisms such as bacteria and fungi.

The carrier can be a solvent or dispersion medium comprising, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion, and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol or sorbitol, and inorganic salts such as sodium chloride in the composition. Prolonged absorption of the injectable compositions can be brought about by including in the composition an agent which delays absorption, for example, aluminum monostearate and gelatin.

Sterile injectable solutions can be prepared by incorporating the active reagent in the required amount in an appropriate solvent with one or a combination of ingredients enumerated above, as required, followed by filtered sterilization. Generally, dispersions are prepared by incorporating at least one compound of the invention into a sterile vehicle that contains a basic dispersion medium and any other required ingredients. In the case of sterile powders for the preparation of sterile injectable solutions, exemplary methods of preparation include vacuum drying and freeze-drying, both of which yield a powder of a compound of the invention plus any additional desired ingredient from a previously sterile-filtered solution thereof.

Oral compositions generally include an inert diluent or an edible carrier. They can be enclosed, for example, in gelatin capsules or compressed into tablets. For the purpose of oral therapeutic administration, the compound of the invention can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition.

For administration by inhalation, the compounds are delivered in the form of an aerosol spray from pressured container or dispenser that contains a suitable propellant, e.g., a gas, such as carbon dioxide, a nebulized liquid, or a dry powder from a suitable device. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active reagents are formulated into ointments, salves, gels, or creams as generally known in the art. The reagents can also be prepared in the form of suppositories (e.g., with conventional suppository bases such as cocoa butter and other glycerides) or retention enemas for rectal delivery.

In one embodiment, the ADH inhibitors, AKR inhibitors, and/or SNO-CoAR inhibitors are prepared with carriers that will protect against rapid elimination from the body. For example, a controlled release formulation can be used, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, suspensions of the compounds of the invention may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also include suitable stabilizers or agents to increase the solubility of the compounds and allow for the preparation of highly concentrated solutions.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of the compound of the invention calculated to produce the desired therapeutic effect in association with the required pharmaceutical carrier. The specification for the dosage unit forms of the invention are dictated by and directly dependent on the unique characteristics of the compound of the invention and the particular therapeutic effect to be achieved, and the limitations inherent in the art of compounding such an active agent for the treatment of individuals.

In some embodiments, the ADH inhibitors, AKR inhibitors, and/or SNO-CoAR inhibitors, including pharmaceutical compositions comprising the ADH inhibitors, AKR inhibitors, and/or SNO-CoAR inhibitors, can be used in methods for preventing or treating (e.g., alleviating one or more symptoms of) medical conditions. The methods comprise administering a therapeutically effective amount of the ADH inhibitors, AKR inhibitors, and/or SNO-CoAR inhibitors to a patient or subject in need thereof. The compositions can also be used for prophylactic therapy.

The patient can be any animal, domestic, livestock, or wild, including, but not limited to cats, dogs, horses, pigs, and cattle, and preferably human patients. As used herein, the terms patient and subject may be used interchangeably.

It will be appreciated that the amount, volume, concentration, and/or dosage of the therapeutic agent that is administered to any one animal or human depends on many factors, including the subject's size, body surface area, age, the particular composition to be administered, sex, time and route of administration, general health, and other drugs being administered concurrently. Specific variations of the above noted amounts, volumes, concentrations, and/or dosages of therapeutic agent can be readily be determined by one skilled in the art using the experimental methods described below.

In some embodiments, the ADH inhibitors, AKR inhibitors, and/or SNO-CoAR inhibitors described herein, can be administered locally and/or systemically to a subject in need thereof at a dose or amount of about 0.1 mol, about 1 mol, about 5 mol, about 10 mol, or more; or about 0.0001 mg/kg, about 0.001 mg/kg, about 0.01 mg/kg, about 0.1 mg/kg, or about 1 mg/kg to about 5 mg/kg or 10 mg/kg of the subject being treated. The ADH inhibitors, AKR inhibitors, and/or SNO-CoAR inhibitors can be administered daily, weekly, biweekly, monthly or less frequently.

In some embodiments, the ADH inhibitors, AKR inhibitors, and/or SNO-CoAR inhibitors can be administered by direct injection using catheterization, such as endo-ventricular catheterization or intra-myocardial catheterization. In one example, a deflectable guide catheter device can be advanced to a left ventricle retrograde across the aortic valve. Once the device is positioned in the left ventricle, the ADH inhibitors, AKR inhibitors, and/or SNO-CoAR inhibitors can be injected into the peri-infarct region (both septal and lateral aspect) area of the left ventricle.

The myocardial tissue of the subject can be imaged prior to administration of the ADH inhibitors, AKR inhibitors, and/or SNO-CoAR inhibitors to define the area of weakened, ischemic, and/or peri-infarct region prior to administration of the ADH inhibitors, AKR inhibitors, and/or SNO-CoAR inhibitors. Defining the weakened, ischemic, and/or peri-infarct region by imaging allows for more accurate targeting of the ADH inhibitors, AKR inhibitors, and/or SNO-CoAR inhibitors to the weakened, ischemic, and/or peri-infarct region. The imaging technique used to define the weakened, ischemic, and/or peri-infarct region of the myocardial tissue can include any known cardio-imaging technique. Such imaging techniques can include, for example, at least one of echocardiography, magnetic resonance imaging, coronary angiogram, electroanatomical mapping, or fluoroscopy. It will be appreciated that other imaging techniques that can define the weakened, ischemic, and/or peri-infarct region can also be used.

In another embodiment, the ADH inhibitors, AKR inhibitors, and/or SNO-CoAR inhibitors can be administered to a subject systemically by intravenous injection or locally at the site of injury, usually within about 24 hours, about 48 hours, about 100 hours, or about 200 hours or more of when an injury occurs (e.g., within about 6 hours, about 12 hours, or 24 hours, inclusive, of the time of the injury).

In some embodiments, the ADH inhibitors, AKR inhibitors, and/or SNO-CoAR inhibitors can administered to a subject for an extended period of time. Sustained administration with the ADH inhibitors, AKR inhibitors, and/or SNO-CoAR inhibitors can be achieved, for example, by repeated administration of the active compound(s) over a period of time, such as one week, several weeks, one month or longer.

In other embodiments, a pharmaceutically acceptable formulation used to administer the therapeutic agent(s) can also be formulated to provide sustained delivery of the active compound to a subject. For example, the formulation may deliver the active compound for at least one, two, three, or four weeks, inclusive, following initial administration to the subject. For example, a subject to be treated in accordance with the method described herein can be treated with the ADH inhibitors, AKR inhibitors, and/or SNO-CoAR inhibitors for at least 30 days (either by repeated administration or by use of a sustained delivery system, or both).

Sustained delivery of the ADH inhibitors, AKR inhibitors, and/or SNO-CoAR inhibitors can be demonstrated by, for example, the continued therapeutic effect of the ADH inhibitors, AKR inhibitors, and/or SNO-CoAR inhibitors over time. Alternatively, sustained delivery of the ADH inhibitors, AKR inhibitors, and/or SNO-CoAR inhibitors may be demonstrated by detecting the presence of the ADH inhibitors, AKR inhibitors, and/or SNO-CoAR inhibitors in vivo over time.

Approaches for sustained delivery include use of a polymeric capsule, a minipump to deliver the formulation, a biodegradable implant, or implanted transgenic autologous cells (see U.S. Pat. No. 6,214,622). Implantable infusion pump systems (e.g., INFUSAID pumps (Towanda, Pa.)); see Zierski et al., 1988; Kanoff, 1994) and osmotic pumps (sold by Alza Corporation) are available commercially and otherwise known in the art. Another mode of administration is via an implantable, externally programmable infusion pump. Infusion pump systems and reservoir systems are also described in, e.g., U.S. Pat. Nos. 5,368,562 and 4,731,058.

Vectors encoding, for example, RNAi constructs (e.g., RNAi expression constructs) described herein that act as the ADH inhibitors, AKR inhibitors, and/or SNO-CoAR inhibitors can often be administered less frequently than other types of therapeutics. For example, an effective amount of such a vector can range from about 0.01 mg/kg to about 5 or 10 mg/kg, inclusive; administered daily, weekly, biweekly, monthly or less frequently.

In some embodiment, the efficacy of the ADH inhibitors, AKR inhibitors, and/or SNO-CoAR inhibitors in treating cardiovascular disorders and diseases, such as congestive heart failure (CHF), cardiac hypertrophy including both atrial and ventricular hypertrophy, myocardial infarction, myocardial ischemia, myocardial ischemia reperfusion injury, cardiomyopathies, or arrhythmias of a subject in need thereof can be measured using, for example, electrocardiogram (ECG) monitoring to determine the electrophysiology of the heart. The ECG measurements can be compared to normal or control ECG measurements to determine efficacy of ADH inhibitors, AKR inhibitors, and/or SNO-CoAR inhibitors in normalizing or restoring electrophysiology of the heart. In some embodiments, ECG can be used in a conjunction with a cardiac stress test or with telemetry.

In other embodiments, a therapeutically effective amount of the ADH inhibitors, AKR inhibitors, and/or SNO-CoAR inhibitors administered to a subject afflicted with a cardiovascular disorder or disease an ADH, AKR, and/or SNO-CoAR inhibiting amount in vivo that causes increase or enhance of protein S-nitrosylation in the heart of a subject protects the subject against a risk associated with the disorder. By way of example, for reperfusion injury, a therapeutically effective amount is a function increasing effective amount or a myocardial cell or cardiomyocyte protective effective amount, e.g., as measured by troponin or CPK.

In other embodiments, the ADH inhibitors, AKR inhibitors, and/or SNO-CoAR inhibitors or a pharmaceutically acceptable salt thereof, or a prodrug or metabolite thereof, can be administered in combination with an NO donor, including SNO-CoA, which is shown to have activity in regulating sterol biosynthesis and CoA metabolism. An NO donor donates nitric oxide or a related redox species and more generally provides nitric oxide bioactivity, that is activity which is identified with nitric oxide, e.g., vasorelaxation or stimulation or inhibition of a receptor protein, e.g., ras protein, adrenergic receptor, NFκB. NO donors including S-nitroso, O-nitroso, C-nitroso, and N-nitroso compounds and nitro derivatives thereof and metal NO complexes, but not excluding other NO bioactivity generating compounds, useful herein are described in "Methods in Nitric Oxide Research," Feelisch et al. eds., pages 71-115 (J. S., John Wiley & Sons, New York, 1996), which is incorporated herein by reference. NO donors which are C-nitroso compounds where nitroso is attached to a tertiary carbon which are useful herein include those described in U.S. Pat. No. 6,359,182 and in WO 02/34705. Examples of S-nitroso compounds, including S-nitrosothiols useful herein, include, for example, S-nitrosoglutathione, S-nitroso-N-acetylpenicillamine, S-nitroso-cysteine and ethyl ester thereof, S-nitroso cysteinyl glycine, S-nitroso-gamma-methyl-L-homocysteine, S-nitroso-L-homocysteine, S-nitroso-gamma-thio-L-leucine, S-nitroso-delta-thio-L-leucine, and S-nitrosoalbumin. Examples of other NO donors useful herein are sodium nitroprusside (nipride), ethyl nitrite, isosorbide, nitroglycerin, SIN 1 which is molsidomine, furoxamines, N-hydroxy(N-nitrosamine), and perfluorocarbons that have been saturated with NO or a hydrophobic NO donor. ADH inhibitors, AKR inhibitors, and/or SNO-CoAR inhibitors can also be combined with R(+) enantiomer of amlodipine, a known NO releaser (Zhang at al., J. Cardiovasc. Pharm. 39: 208-214 (2002)).

In some embodiments, the ADH inhibitors, AKR inhibitors, and/or SNO-CoAR inhibitors can be administered in a combinatorial therapy or combination therapy that includes administration of the ADH inhibitors, AKR inhibitors, and/or SNO-CoAR inhibitors with one or more additional active agents. The phrase "combinatorial therapy" or "combination therapy" embraces the administration of the ADH inhibitors, AKR inhibitors, and/or SNO-CoAR inhibitors, and one or more therapeutic agents as part of a specific treatment regimen intended to provide beneficial effect from the co-action of these therapeutic agents. Administration of these therapeutic agents in combination typically is carried out over a defined period (usually minutes, hours, days or weeks depending upon the combination selected). "Combinatorial therapy" or "combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example by administering to the subject an individual dose having a fixed ratio of each therapeutic agent or in multiple, individual doses for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissue. The therapeutic agents can be administered by the same route or by different routes. The sequence in which the therapeutic agents are administered is not narrowly critical.

In some embodiments, the ADH inhibitors, AKR inhibitors, and/or SNO-CoAR inhibitors can be administered in combination with active agents, such as vasodilators, prostanoid agonists, antiandrogens, cyclosporins and their analogues, antimicrobials, triterpenes, alone or as a mixture. The vasodilators can include potassium channel agonists including minoxidil and its derivatives, aminexil and the compounds described in U.S. Pat. Nos. 3,382,247, 5,756,092, 5,772,990, 5,760,043, 5,466,694, 5,438,058, 4,973,474, chromakalin and diazoxide. The antiandrogens can include 5α-reductase inhibitors such as finasteride and the compounds described in U.S. Pat. No. 5,516,779, cyprosterone acetate, azelaic acid, its salts and its derivatives, and the compounds described in U.S. Pat. No. 5,480,913, flutamide and the compounds described in U.S. Pat. Nos. 5,411,981, 5,565,467 and 4,910,226. The antimicrobial compounds can include selenium derivatives, ketoconazole, triclocarban, triclosan, zinc pyrithione, itraconazole, pyridine acid, hinokitiol, mipirocine, and the compounds described in EP 680745, clinycine hydrochloride, benzoyl or benzyl peroxide and minocycline. The anti-inflammatory agents can include inhibitors specific for Cox-2 such as for example NS-398 and DuP-697 (B. Batistini et al., DN&P 1994; 7(8):501-511) and/or inhibitors of lipoxygenases, in particular 5-lipoxygenase, such as for example zileuton (F. J. Alvarez & R. T. Slade, Pharmaceutical Res. 1992; 9(11): 1465-1473).

Other active compounds, which can be present in pharmaceutical compositions can include aminexil and its derivatives, 60-[(9Z,12Z)octadec-9,12-dienoyl]hexapyranose, benzalkonium chloride, benzethonium chloride, phenol, oestradiol, chlorpheniramine maleate, chlorophyllin derivatives, cholesterol, cysteine, methionine, benzyl nicotinate, menthol, peppermint oil, calcium panthotenate, panthenol, resorcinol, protein kinase C inhibitors, prostaglandin H synthase 1 or COX-1 activators, or COX-2 activators, glycosidase inhibitors, glycosaminoglycanase inhibitors, pyroglutamic acid esters, hexosaccharidic or acylhexosaccharidic acids, substituted ethylenearyls, N-acylated amino acids, flavonoids, derivatives and analogues of ascomycin, histamine antagonists, triterpenes, such as ursolic acid and the compounds described in U.S. Pat. Nos. 5,529,769, 5,468,888, 5,631,282, saponins, proteoglycanase inhibitors, agonists and antagonists of oestrogens, pseudopterins, cytokines and growth factor promoters, IL-1 or IL-6 inhibitors, IL-10 promoters, TNF inhibitors, vitamins, such as vitamin D, analogues of vitamin B12 and panthotenol, hydroxy acids, benzophenones, esterified fatty acids, and hydantoin.

It will also be appreciated that certain selective ADH inhibitors, AKR inhibitors, and/or SNO-CoAR inhibitors that inhibit some ADHs, AKRs, and/or SNO-CoARs can be administered in combination with other selective ADH inhibitors, AKR inhibitors, and/or SNO-CoAR inhibitors that inhibit other ADHs, AKRs, and/or SNO-CoARs. For example, a selective ADH6 inhibitor can be administered in combination with an ADH3 inhibitor.

In one embodiment, the ADH inhibitors, AKR inhibitors, and/or SNO-CoAR inhibitors can be administered in combination with an agent that imposes nitrosative or oxidative stress. Agents for selectively imposing nitrosative stress to inhibit proliferation of pathologically proliferating cells in combination therapy with the ADH inhibitors, AKR inhibitors, and/or SNO-CoAR inhibitors and dosages and routes of administration therefor include those disclosed in U.S. Pat. No. 6,057,367, which is incorporated herein. Supplemental agents for imposing oxidative stress (i.e., agents that increase GSSG (oxidized glutathione) over GSH (glutathione) ratio or NAD(P) over NAD(P)H ratio or increase thiobarbituric acid derivatives) in combination therapy with the ADH inhibitors, AKR inhibitors, and/or SNO-CoAR inhibitors include, for example, L-buthionine-S-sulfoximine (BSO), glutathione reductase inhibitors (e.g., BCNU), inhibitors or uncouplers of mitochondrial respiration, and drugs that increase reactive oxygen species (ROS), e.g., adriamycin, in standard dosages with standard routes of administration.

The ADH inhibitors, AKR inhibitors, and/or SNO-CoAR inhibitors may also be co-administered with a phosphodiesterase inhibitor (e.g., rolipram, cilomilast, roflumilast, VIAGRA (sildenifil citrate), CLAUS (tadalafil), LEVITRA (vardenifil), etc.), a β-agonist, a steroid, or a leukotriene antagonist (LTD-4). Those skilled in the art can readily determine the appropriate therapeutically effective amount depending on the disorder to be ameliorated.

The invention is further illustrated by the following example, which is not intended to limit the scope of the claims.

EXAMPLE

Figure 1B:
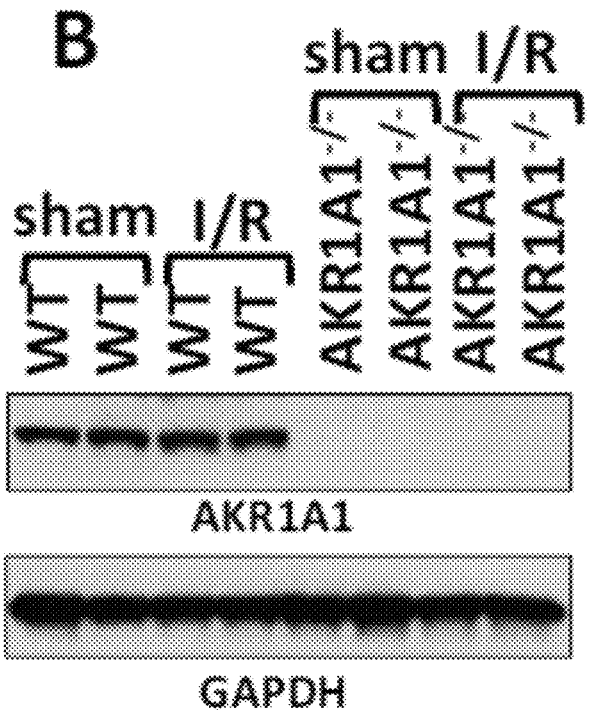
Figure 1C:
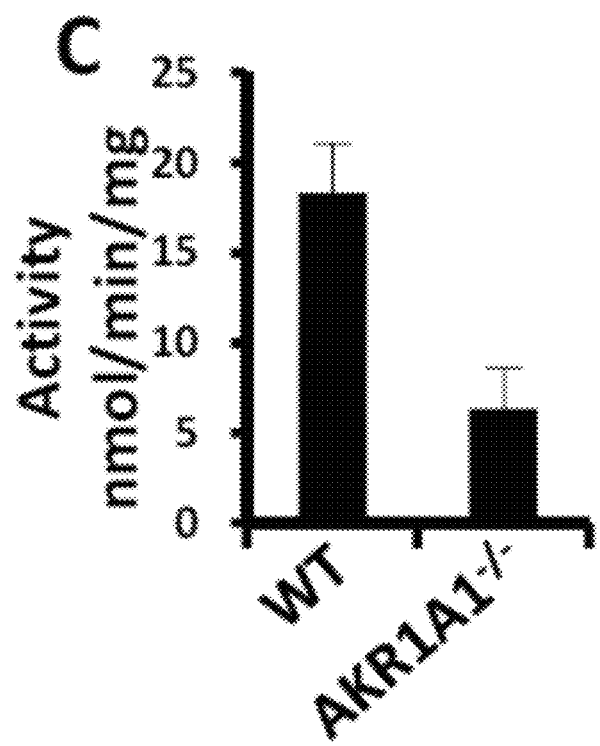
Figure 1D:
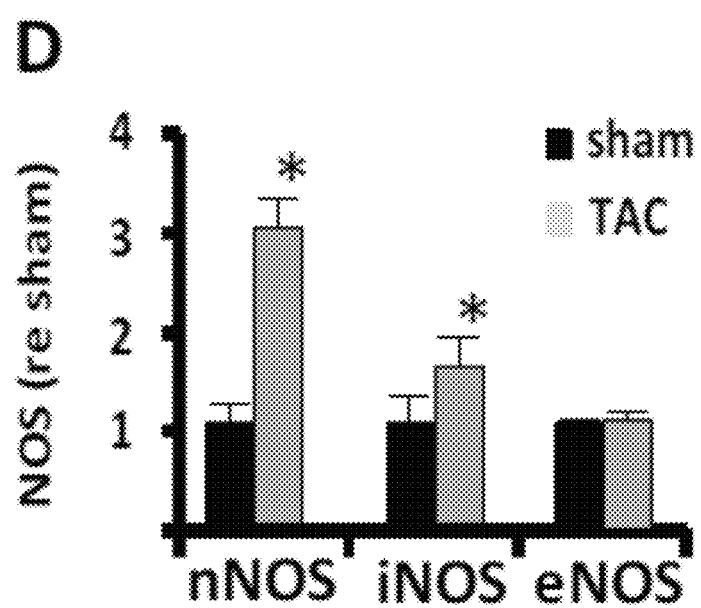

Generation of AKR1A1$^{-/-}$ Mice, AKR1A1$^{-/-}$/eNOS$^{-/-}$ Mice and AKR1A1$^{-/-}$/iNOS$^{-/-}$ Mice To investigate the physiological role of AKR1A1 in mouse, we generated the AKR1A1-knockout mice (AKR1A1$^{-/-}$), which have body weight similar to those of wild-type (WT) mice after 9-11 weeks (FIG. 1A). AKR1A1 is highly expressed in heart of WT mice, but completely absence in heart of AKR1A1$^{-/-}$ (FIG. 1B). SNO-CoA metabolizing activity is dramatically reduced in the heart of AKR1A1$^{-/-}$ (FIG. 1C), which suggests that AKR1A1 is a major SNO-CoA reductase in the mouse heart. In order to investigate whether the physiological role of AKR1A1 is dependent on nitric oxide pathway, we generated double-knockout mice AKR1A1$^{-/-}$/eNOS$^{-/-}$ mice and AKR1A1$^{-/-}$/iNOS$^{-/-}$ mice, which have body weights similar to those of WT mice after 9-11 weeks (FIG. 1A).

AKR1A1$^{-/-}$ Mice Display Greater Cardioprotection Against MI/R than WT Mice

Figure 2G:
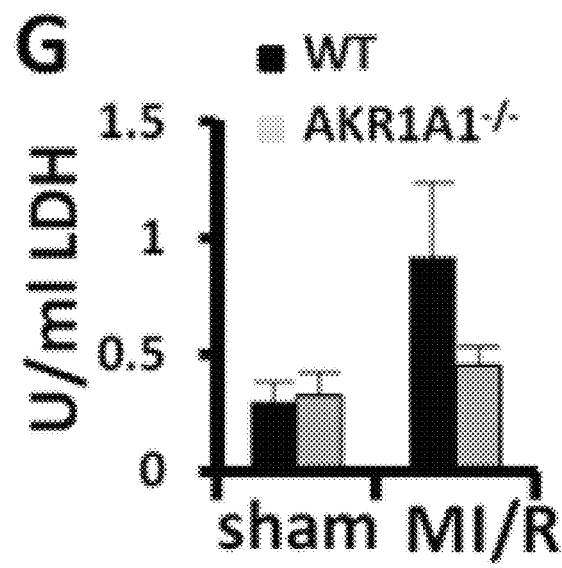
FIG. 2(A-I) illustrate knockout of AKR1A1 in mice protects heart against MI/R. (A) Successful myocardial I/R injury. (B) Myocardial infarct size after MI/R. Infarcted tissue is white, the rest of the area at risk is grey, and non-risk tissue is dark grey. (C) Quantification of the myocardial infarct size after MI/R injury (24-hour reperfusion). AON is expressed as a percentage of the LV (left ventricle) and AAR. (D-E) Quantification of left ventricular function after MI/R injury (24-hour reperfusion). EF, FS, and LVID-s are determined by Echocardiography. (F-G) TnT and LDH concentration in blood after MI/R injury (4-hour reperfusion). (H) TUNEL staining after MI/R injury (4-hour reperfusion). Arrows indicate TUNEL-positive nucleus. (I) Concentration of cGMP after MI/R injury (10-minute reperfusion).
Figure 2H:
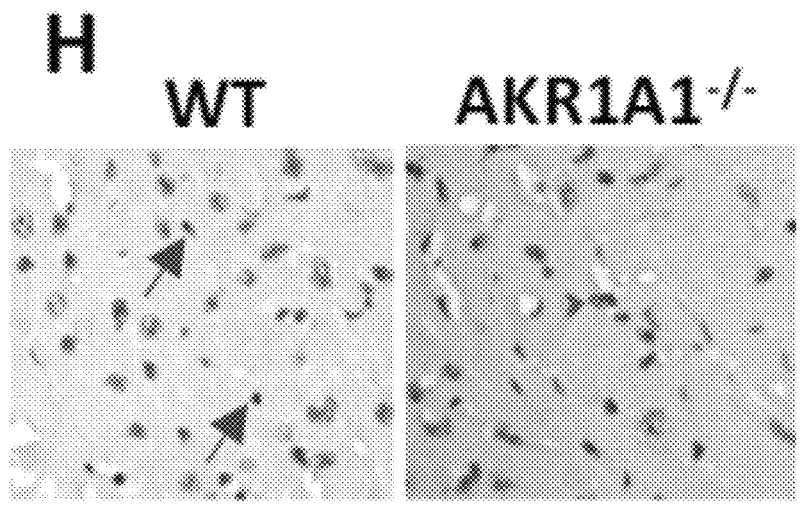
Figure 2I:
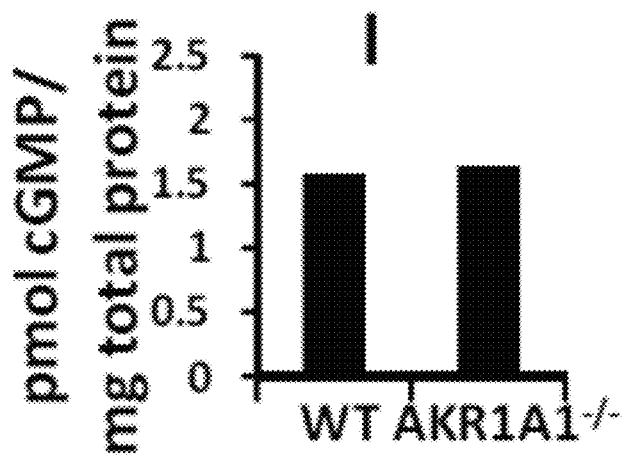

We first studied the physiological role of AKR1A1 in MI/R using AKR1A1$^{-/-}$ mice (FIG. 2A). We used Evens blue/triphenyltetrazolium chloride (TTC)-staining, echocardiography, diagnosis biomarker, histopathological analysis to illustrate the cardiac function after left anterior descending (LAD) coronary artery ligation for 30 minutes and reperfusion for certain time based on experimental requirements. Procured hearts after 24-hour reperfusion were explanted and infused with Evens blue to demarcate the ischemic area susceptible to infarction (defined as the area at risk or AAR), and counter-stained with triphenyltetrazolium chloride (TTC) to identify infarcted regions within the AAR (defined as the area of necrosis or AON). Representative hearts from both strains are presented in FIG. 2B. AKR1A1$^{-/-}$ mice had a significantly smaller proportion of infarcted myocardium compared to WT mice (FIG. 2C). Consistent with the lower levels of injury exhibited by AKR1A1$^{-/-}$ mice, echocardiography data revealed that preserved left ventricular function was characterized by significantly higher measures of ejection fraction (EF) and fractional shortening (FS) in AKR1A1$^{-/-}$ mice than in WT mice (FIG. 2D). On the contrary, left ventricular internal diameter end diastole (LVID-s) is significantly lower in AKR1A1$^{-/-}$ mice than in WT mice (FIG. 2E). We measured levels of cardiac troponin I (TnT) and lactate dehydrogenase (LDH) in blood, which are two critical diagnosis biomarkers of MI/R. Both TnT and LDH level were significantly lower in AKR1A1$^{-/-}$ mice than in WT mice, which indicates that AKR1A1$^{-/-}$ mice more successfully tolerate MI/R injury (FIG. 2F,G). In order to observe cellular damage after MI/R, we performed immunohistochemistry with TUNEL staining. Representative staining images of MI/R-damaged heart tissues demonstrated that cardiomyocytic apoptosis occurred more in WT mice than in AKR1A1$^{-/-}$ mice (FIG. 2H). To investigate whether cardioprotection mediated by knockout of AKR1A1 is dependent on cGMP pathway, we measured the level of cGMP in WT and AKR1A1$^{-/-}$ mice after MI/R using cGMP kit from Sigma. The amount of cGMP in WT mice is same as in AKR1A1$^{-/-}$ mice, suggesting this cardioprotection mediated by knockout of AKR1A1 is independent on cGMP pathway (FIG. 2I).

Figure 3A:
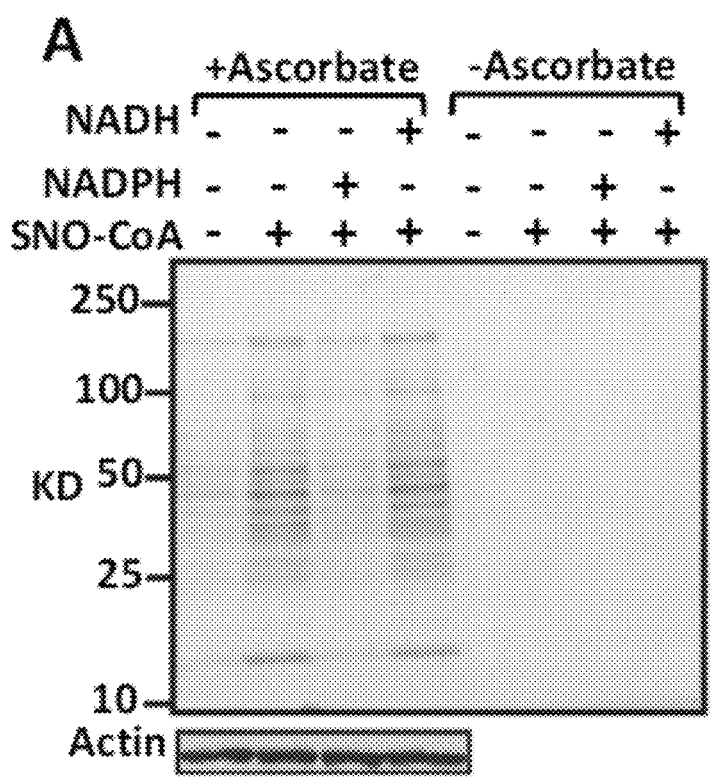
FIG. 3(A-B) illustrate SNO-CoA and AKR1A1 regulate proteins S-nitrosylation. (A) SNO-CoA-mediated protein S-nitrosylation. Representative Coomassie-stained SDS/PAGE gels displaying SNO proteins isolated by SNO-RAC following incubation of mice extract (1 mg/mL in 1 mL of reaction volume) for 10 min with SNO-CoA (60 μM) alone or in combination with NADPH or NADH (100 μM). Abcprbate (Asc) was omitted from the SNO-RAC assay as a specificity control. (B) S-nitrosylated proteins in ischemic/reperfusion-damaged heart of AKR1A1$^{-/-}$ mice.
Figure 3B:
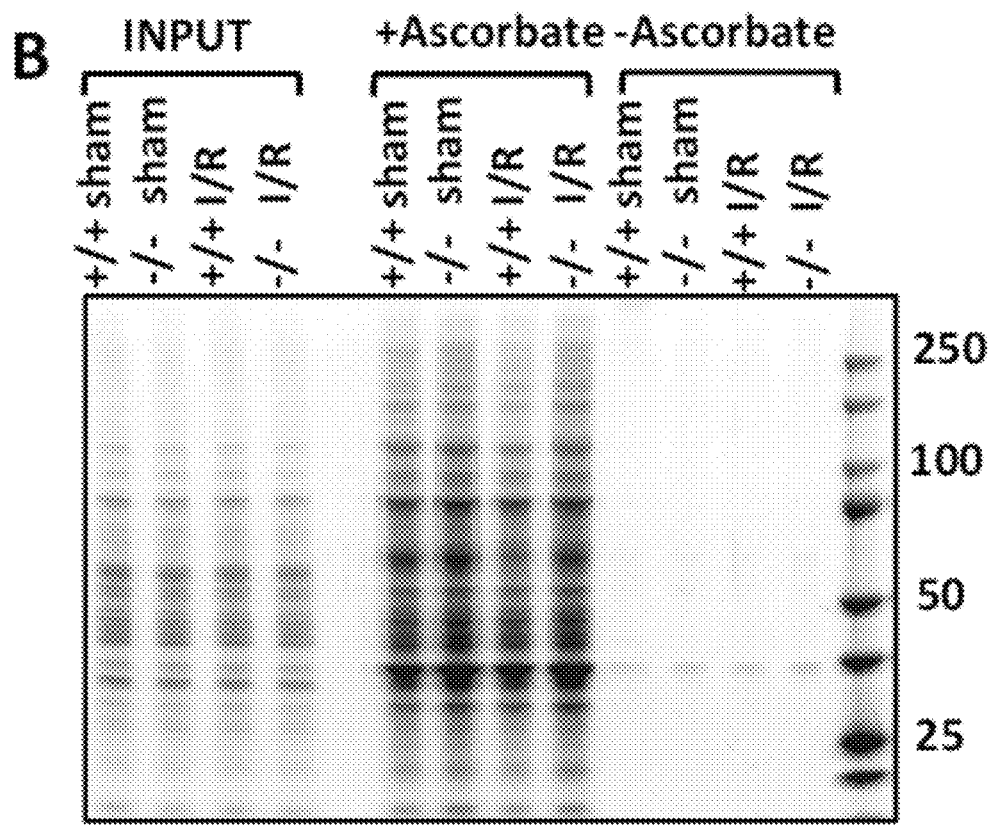

Protein S-Nitrosylation is Increased in Heart of AKR1A1−/− Mice after MI/R Surgery Addition of SNO-CoA to extract of mouse tissue led to the S-nitrosylation of numerous proteins, and then co-addition of NADPH—but not NADH—markedly diminished SNO-protein formation (FIG. 3A). In addition, we found that SNO level of proteins was much higher in the I/R-damaged heart of AKR1A1 regulates the S-nitrosylation of proteins in vivo. In contrast, AKR1A1 mice and WT mice have similar SNO level of proteins in sham-treated hearts (FIG. 3B), which suggests that S-nitrosylation of proteins manipulated by AKR1A1 plays an important role in stage of ischemic/reperfusion injury.

Interactome of AKR1A1

Figure 4:
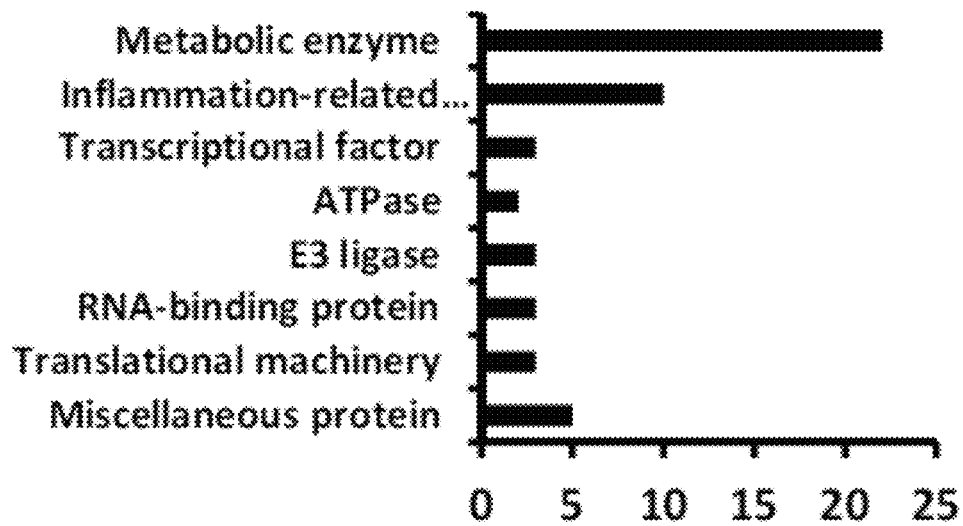
FIG. 4 illustrates interactome of AKR1A1 in mouse cells.

We characterized the AKR1A1 interactome in the mouse cells with anti-AKR1A1 primary antibody. There are total 51 proteins identified in the complex. Functional enrichment analysis of the 51 proteins has showed that 22 proteins are enzymes participating in a broad spectrum of metabolic pathways, including glycolysis and the pentose phosphate pathway (FIG. 4).

Figure 5A:
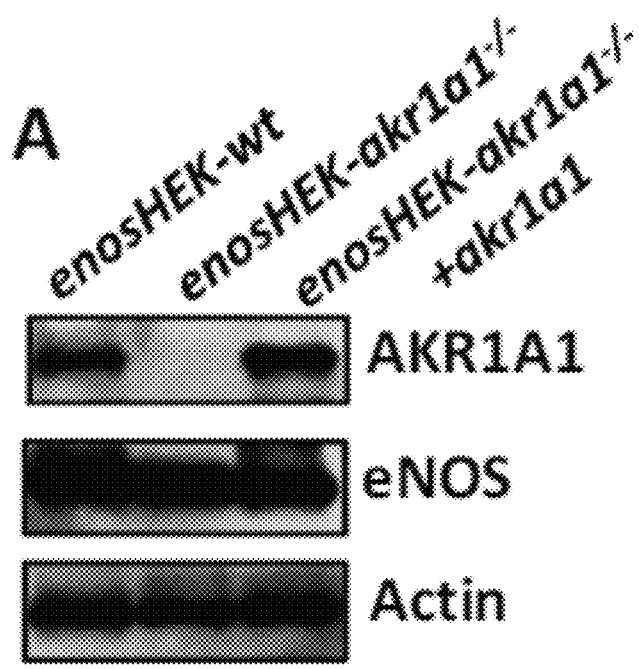
FIG. 5(A-F) illustrate knockout of AKR1A1 activates antioxidant system. (A) Establishment of two HEK293 cell lines. enosHEK-akr1a1$^{-/-}$: AKR1A1 gene is deleted in HEK293 using crisper-cas9 method. enosHEKakr1a1$^{-/-}$+akr1a1: stably overexpressing exogenous AKR1A1 in enosHEK-akr1a1$^{-/-}$ cell lines. (B-D) The amount of $H_2O_2$, GSSG/GSH ratio, and NADPH/NADP+ ratio in three cell lines were measured at the indicated time points after cisplatin (20 μM) treatment. (E-F) GSSG/GSH and NADPH/NADP+ ratio were measured in WT and AKR1A1$^{-/-}$ mice.
Figure 5B:
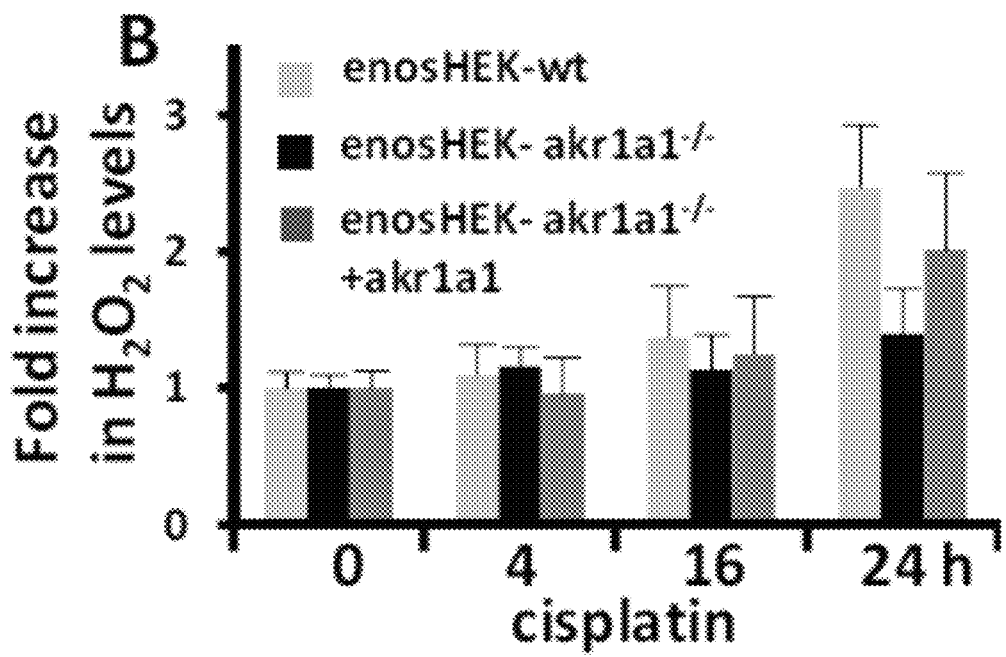
Figure 5C:
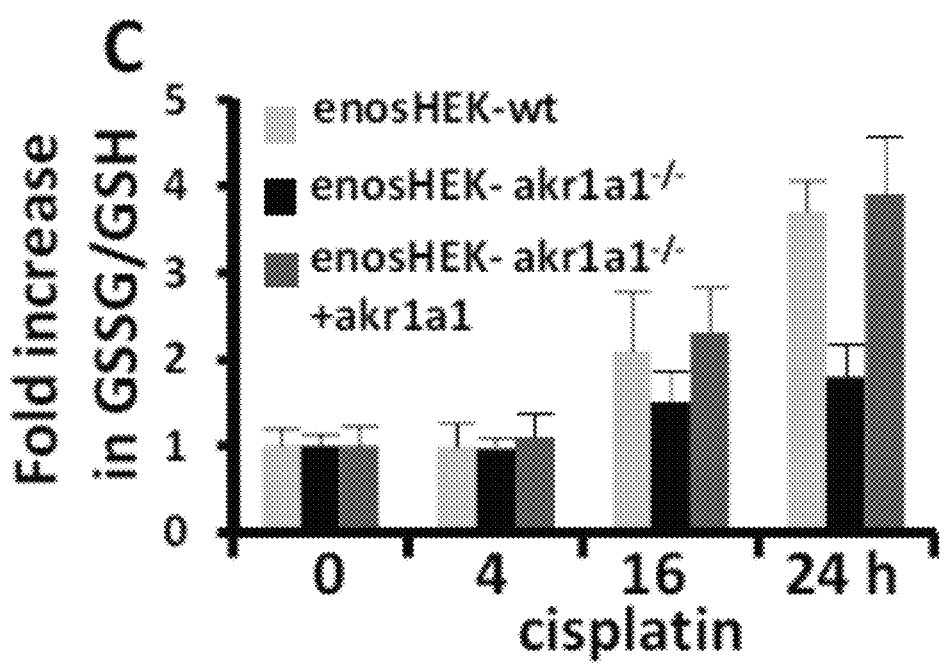
Figure 5D:
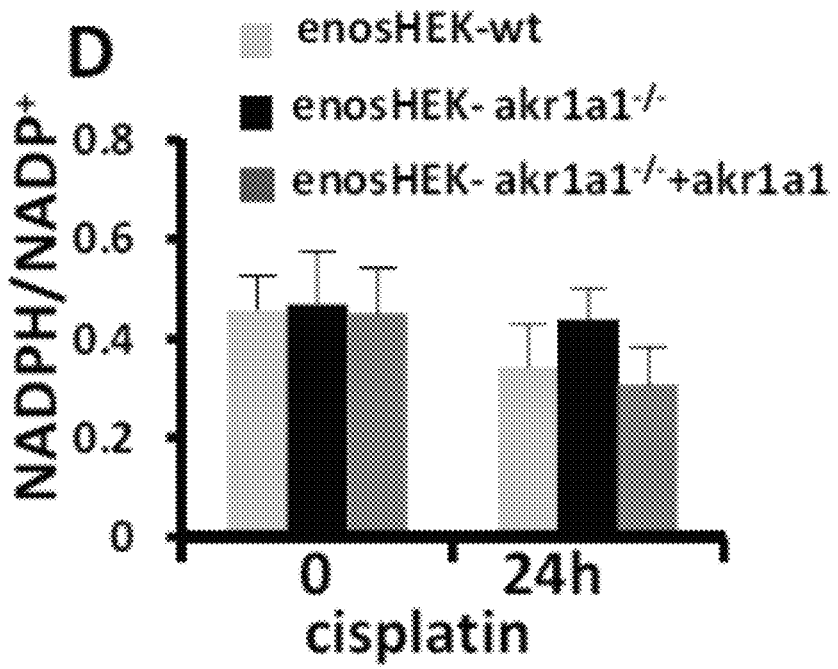
Figure 5E:
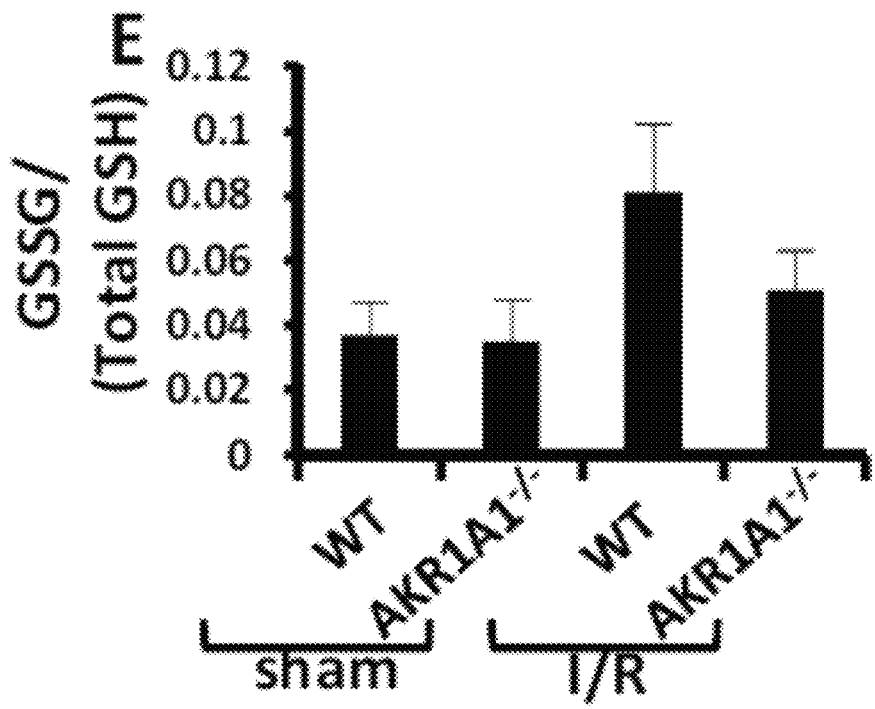
Figure 5F:
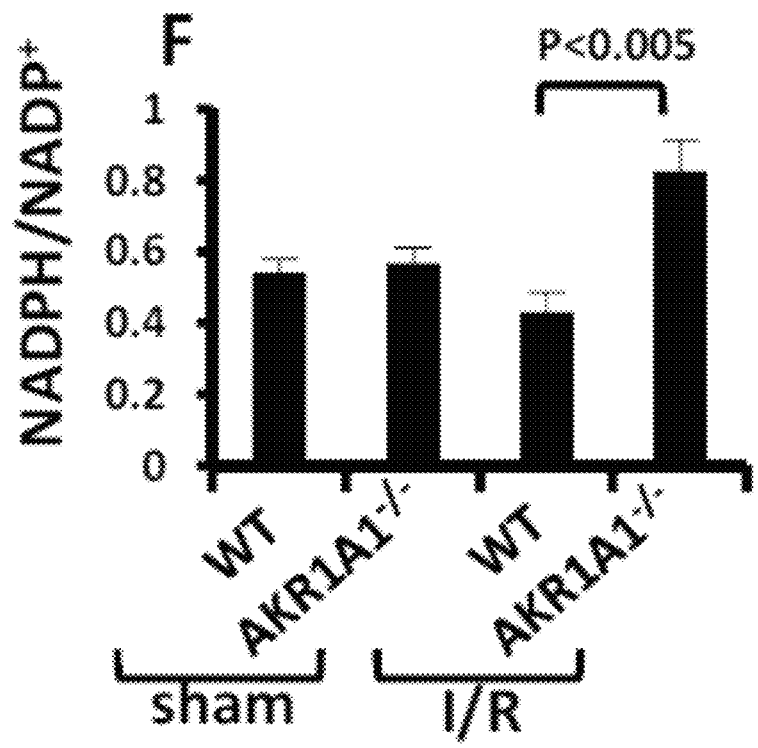

We found that the amount of $H_2O_2$ and the GSSG/GSH ratio, which are two important indicators of oxidative stress in cells, were lower in enosHEK-AKR1A1−/− cells than enosHEK-wt cells after 20 μM cisplatin treatment for 24 h. Expression of exogenous AKR1A1 in enosHEK-AKR1A1−/− cells returned the GSSG/GSH ratio and $H_2O_2$ to normal levels, which suggests that AKR1A1 plays an important role in protecting against the toxicity of reactive oxygen species in HEK293 cells (FIGS. 5A, 5B, 5C). We also found that the GSSG/GSH ratio was lower in AKR1A1−/− mice than in WT mice (FIG. 5D). NADPH is used to convert oxidized glutathione (GSSG) to reduced GSH, and enhancement of NADPH generation can ameliorate cardiac injury in model of MI/R. Therefore we examined the NADPH/NADP+ ratio in AKR1A1-knockout HEK293 cells and mice. We found that the NADPH/NADP+ ratio was higher in AKR1A1-knockout HEK293 cells or mice than in WT cells or WT mice (FIGS. 5E, 5F).

Compounds Efficiently Inhibit AKR1A1 to Reduce SNO-CoA Both In Vitro and Vivo

Figure 6A:
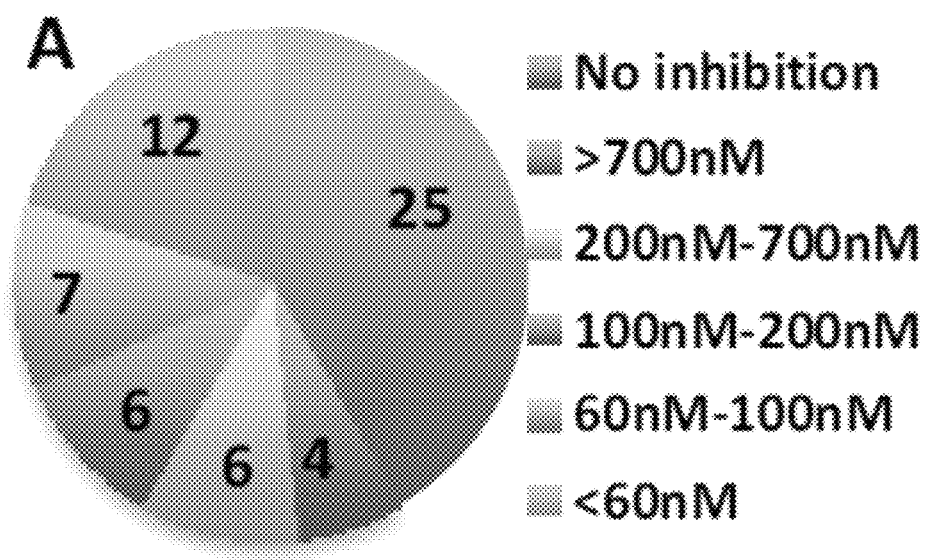
FIG. 6(A-C) illustrate screening the inhibitors of AKR1A1. (A) IC$_{50}$ of sixty compounds to inhibit activity of AKR1A1. (B) A selective AKR1A1 inhibits recombinant AKR1A1 to reduce SNO-CoA in vitro. (C) The selective AKR1A1 inhibitor inhibits endogenous AKR1A1 to reduce SNO-CoA in mice heart.

In order to discover most efficient compounds to inhibit SNO-CoA-reductase activity of purified AKR1A1, We in silico designed sixty compounds based on structure of AKR1A1 and synthesized them. We investigated half-maximal inhibitory concentration ($IC_{50}$) of all of compounds in inhibition of purified AKR1A1 activity, and found that $IC_{50}$ of numerous imirestat analogues are below 60 nM (FIG. 6A). We used the following imirestat analogue as an example to further test their inhibitory efficiency:

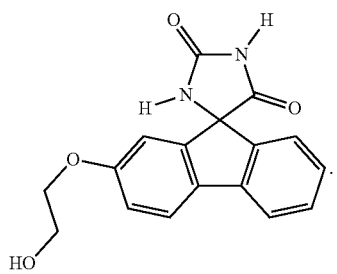 [SMILES: O=C1NC(=O)C2(N1)c1ccccc1-c1ccc(OCCO)cc12]

Figure 6B:
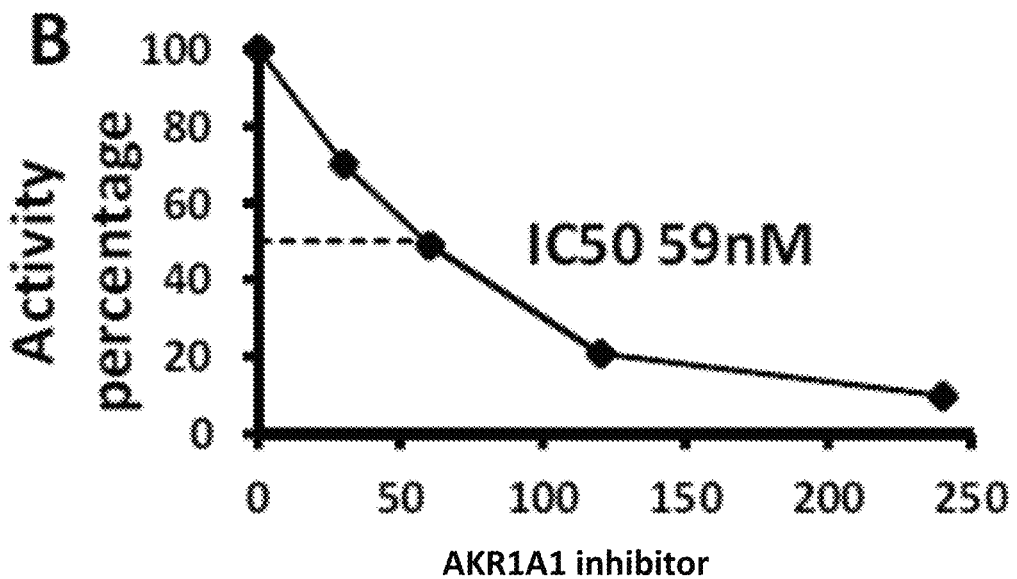
Figure 6C:
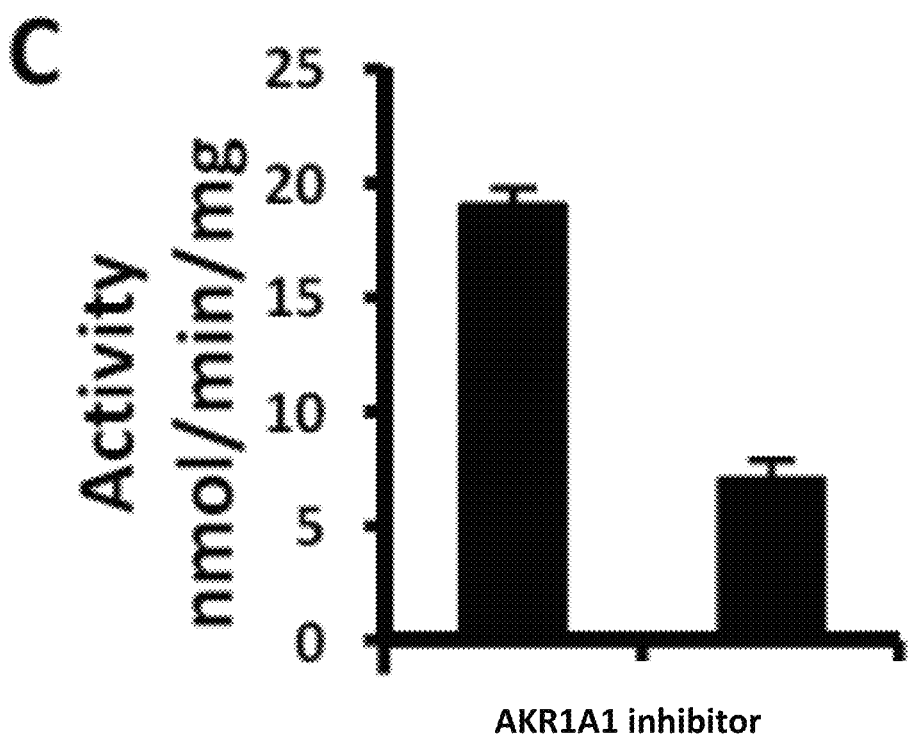

The compound efficiently inhibited the SNO-CoA-reductase activity of AKR1A1 in vitro (FIG. 6B). To investigate effect of the compound on activity of endogenous AKR1A1, we intraperitoneally injected DMSO or the compound (dissolved in DMSO, 20 mg/kg body weight) into mice and measured SNO-CoA-reductase activity in heart lysis after 16-hour injection. SNO-CoA-reductase activity in heart treated by the compound is reduced about 70% compared with those in heart treated by DMSO (FIG. 6C).

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A method of treating myocardial ischemia reperfusion injury in a subject in need thereof, the method comprising:
administering to the subject an AKR1A1 inhibitor at an amount effective to promote S-nitrosylation of proteins in the subject and treat myocardial ischemia reperfusion injury in the subject, wherein the AKR1A1 inhibitor has an AKR1A1 $IC_{50} \leq 100$ nm, wherein the AKR1A1 inhibitor is imirestat

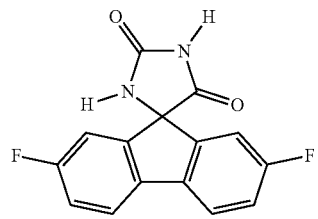 [SMILES: O=C1NC(=O)C2(N1)c1cc(F)ccc1-c1ccc(F)cc12]

or an imirestat analogue compound selected from the group consisting of:

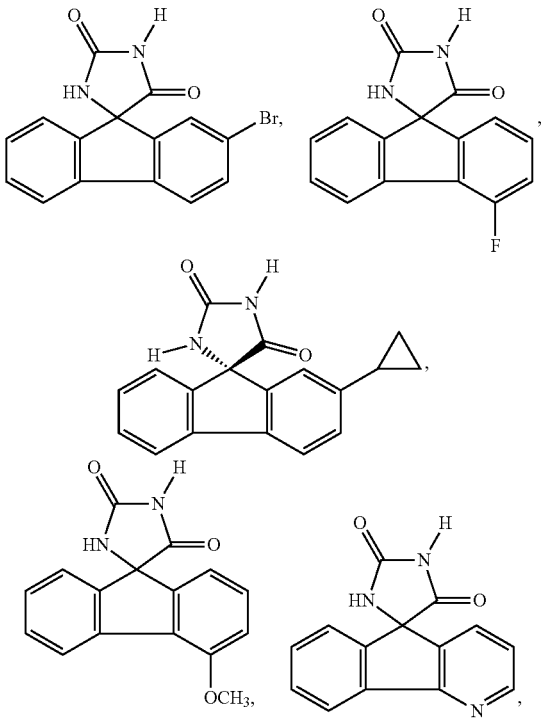

-continued
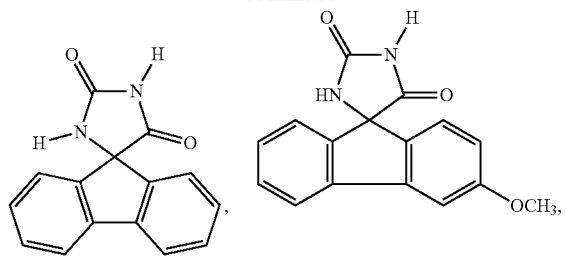
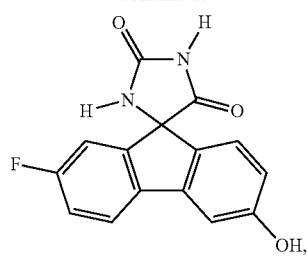
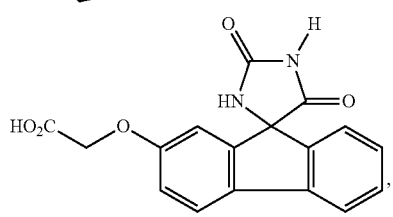
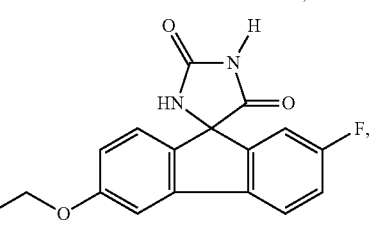
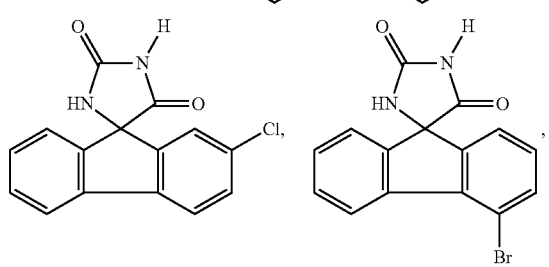
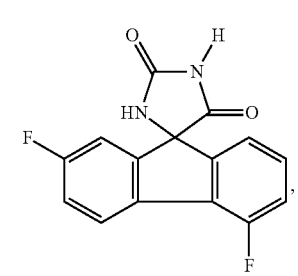
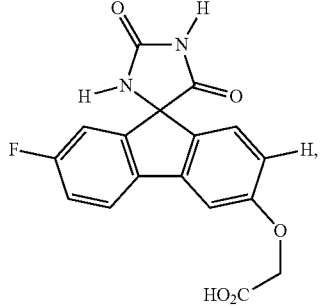
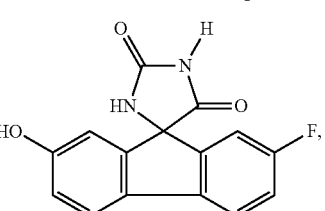
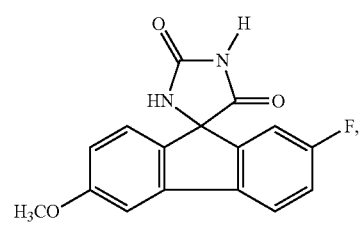
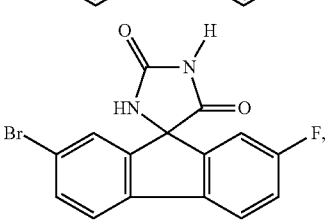
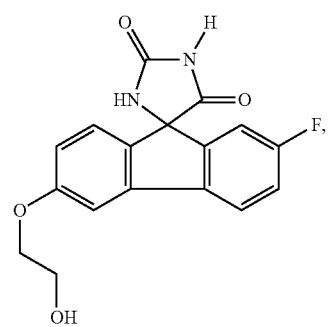
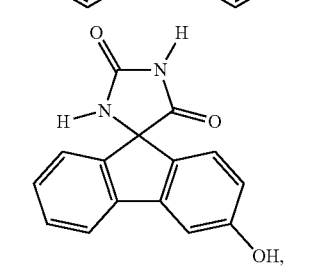
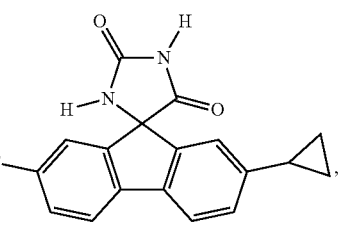

53
-continued

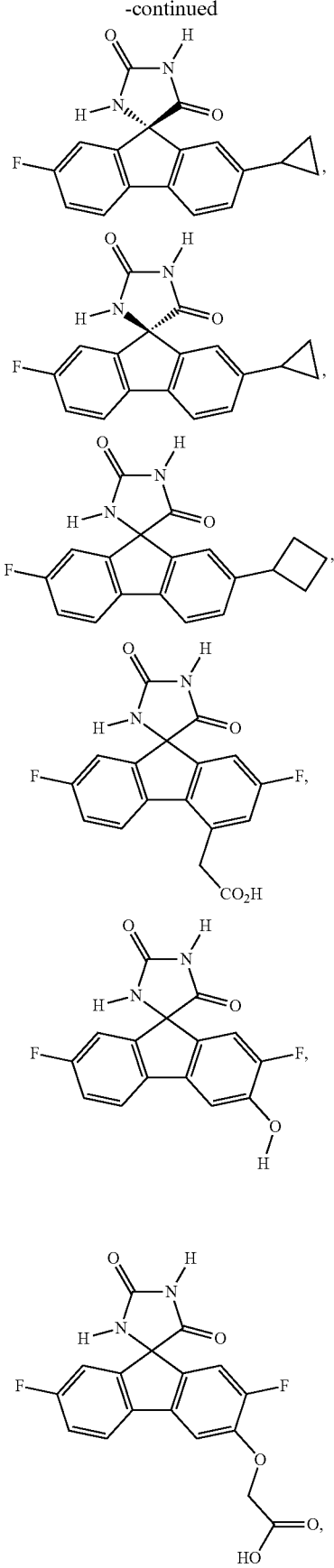

54
-continued

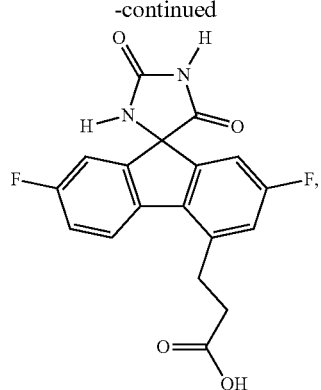

and pharmaceutically acceptable salts thereof.

2. The method of claim 1, wherein a selective or partially selective AKR1A1 inhibitor is administered in combination with a selective or partially selective AKR1B1 inhibitor.

3. The method of claim 2, wherein the AKR1B1 inhibitor can have a selectivity for AKR1B1 versus AKR1A1≥2 times.

4. A method of treating myocardial ischemia reperfusion injury in a subject in need thereof, the method comprising:
administering to the subject an AKR1A1 inhibitor at an amount effective to promote S-nitrosylation of proteins in the subject and treat myocardial ischemia reperfusion injury in the subject, wherein the AKR1A1 inhibitor has an AKR1A1 IC$_{50}$≤100 nm, wherein the AKR1A1 inhibitor is an imirestat analogue compound selected from the group consisting of:

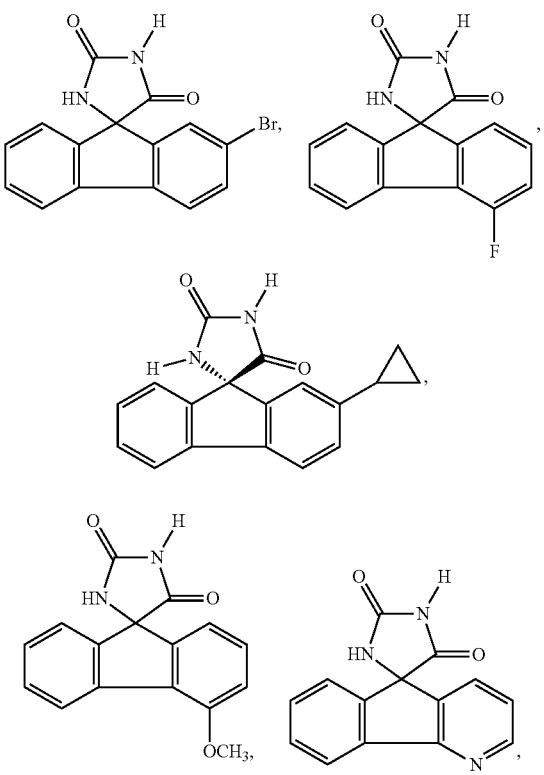

-continued
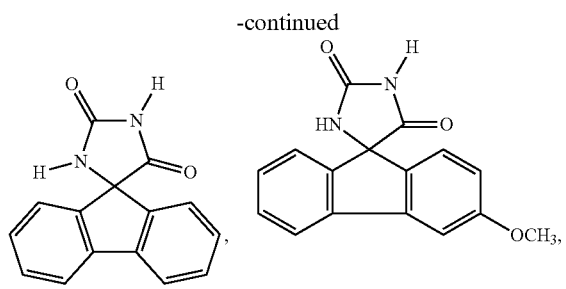
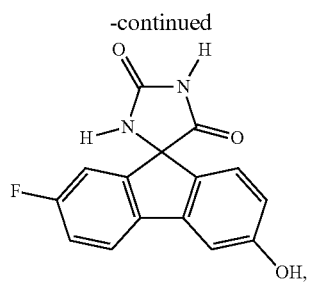
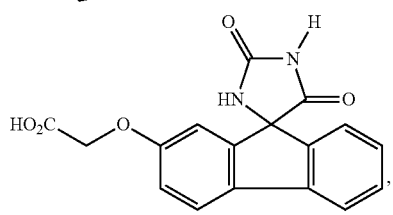
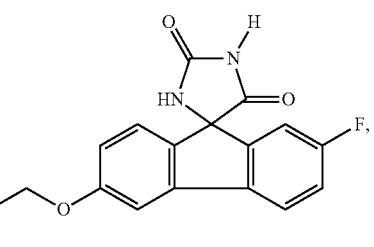
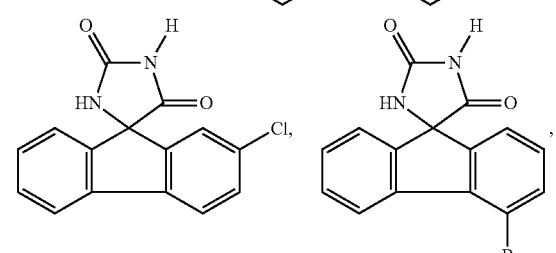
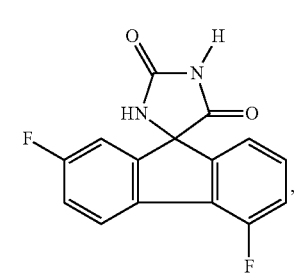
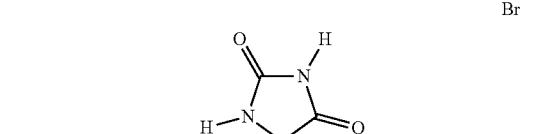
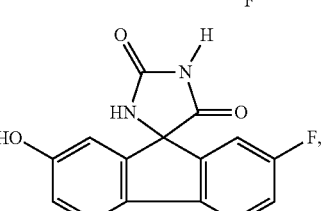
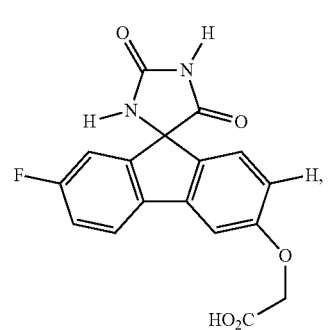
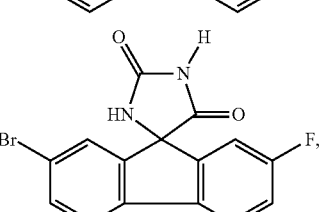
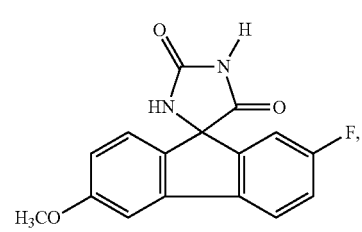
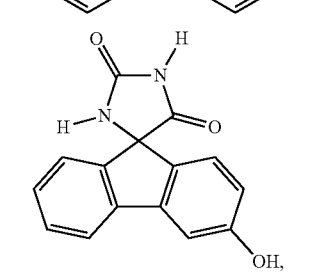
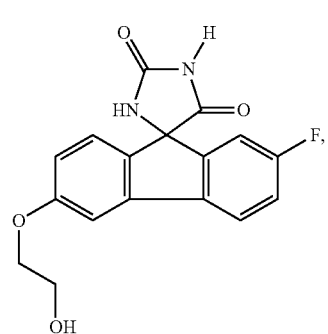
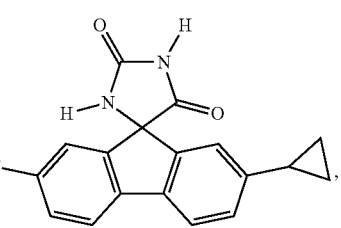

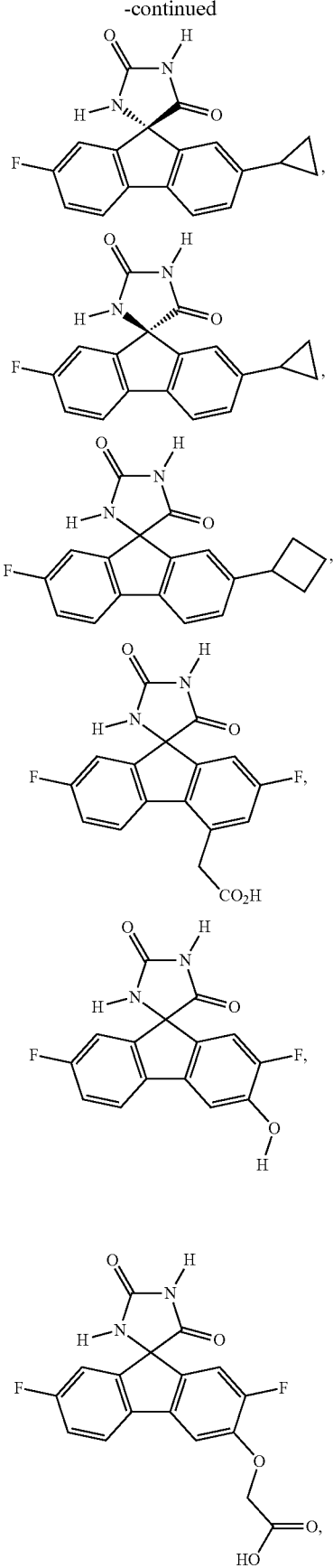

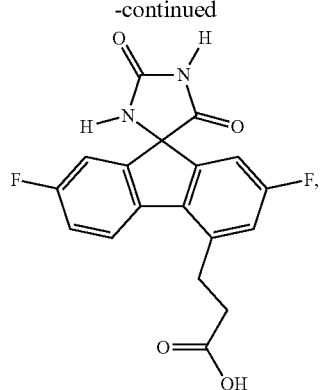

and pharmaceutically acceptable salts thereof.

5. A method of treating myocardial ischemia reperfusion injury in a subject in need thereof, the method consisting of:

administering to the subject an AKR1A1 inhibitor at an amount effective to promote S-nitrosylation of proteins in the subject and treat myocardial ischemia reperfusion injury in the subject, wherein the AKR1A1 inhibitor has an AKR1A1 $IC_{50} \leq 100$ nm, wherein the AKR1A1 inhibitor is imirestat

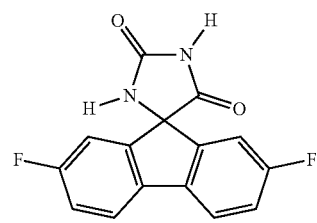 [SMILES: O=C1NC(=O)C2(N1)c1cc(F)ccc1-c1ccc(F)cc12]

or an imirestat analogue compound selected from the group consisting of:

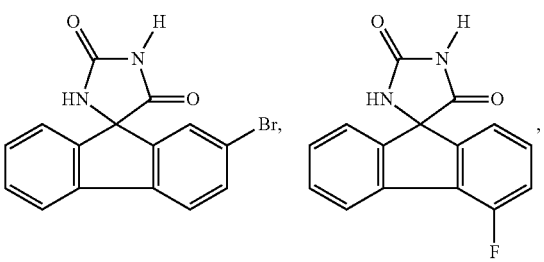

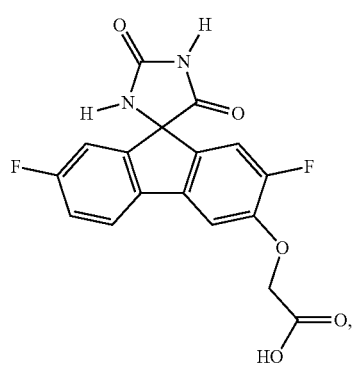

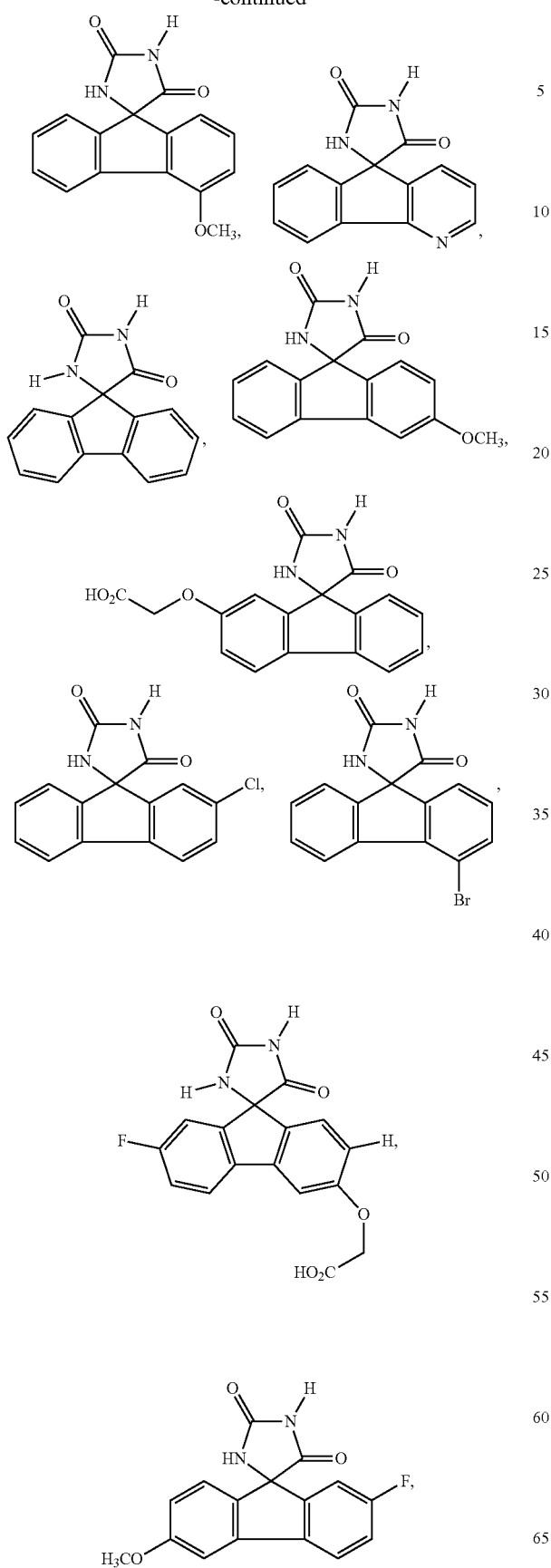
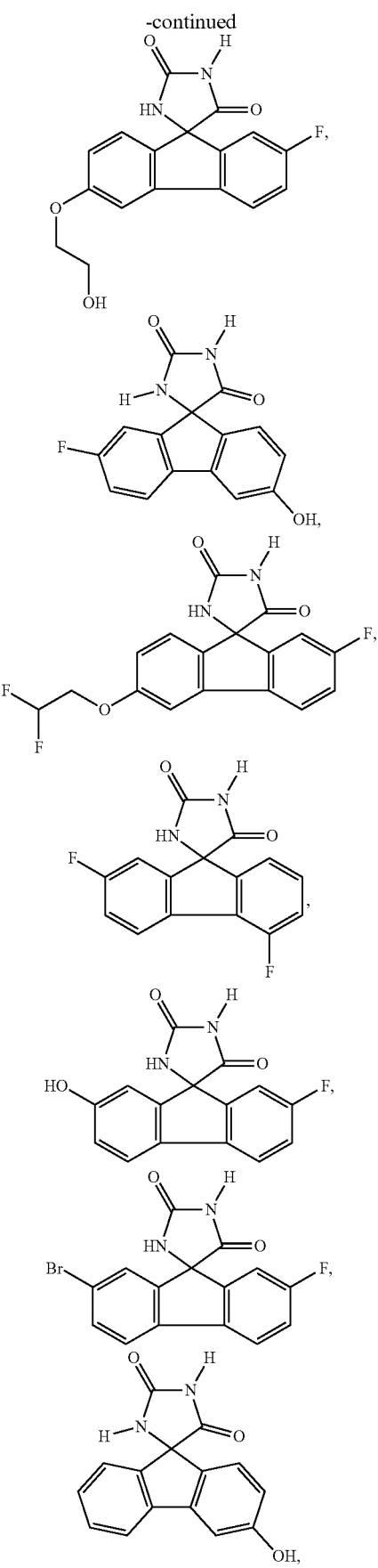

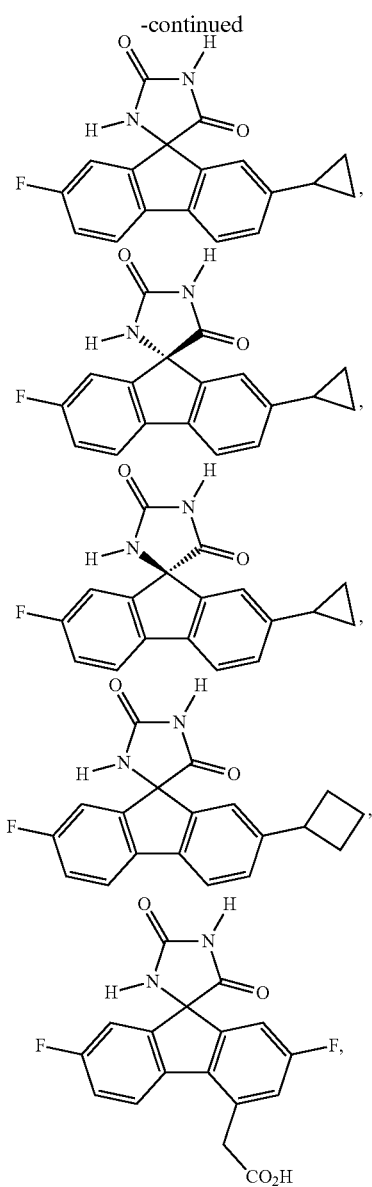
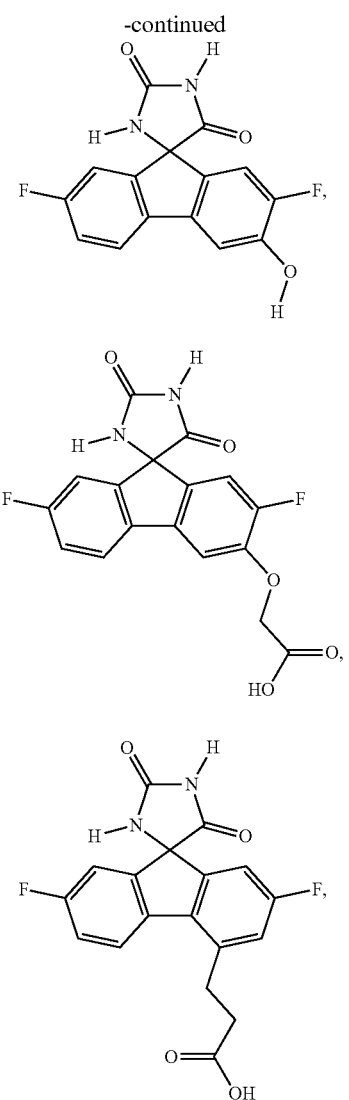
and pharmaceutically acceptable salts thereof.
* * * * *